(12) United States Patent
Lurie et al.

(10) Patent No.: US 11,020,313 B2
(45) Date of Patent: *Jun. 1, 2021

(54) SYSTEMS AND METHODS TO INCREASE SURVIVAL WITH FAVORABLE NEUROLOGICAL FUNCTION AFTER CARDIAC ARREST

(71) Applicant: ZOLL Medical Corporation, Chelmsford, MA (US)

(72) Inventors: Keith G. Lurie, Minneapolis, MN (US); Anja Metzger, Stillwater, MN (US)

(73) Assignee: ZOLL Medical Corporation, Chelmsford, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/596,097

(22) Filed: Oct. 8, 2019

(65) Prior Publication Data

US 2020/0069514 A1  Mar. 5, 2020

Related U.S. Application Data

(63) Continuation of application No. 15/158,738, filed on May 19, 2016, now Pat. No. 10,478,374, which is a
(Continued)

(51) Int. Cl.
*A61H 31/00* (2006.01)
*A61M 16/00* (2006.01)
(Continued)

(52) U.S. Cl.
CPC ......... *A61H 31/007* (2013.01); *A61H 31/004* (2013.01); *A61H 31/005* (2013.01);
(Continued)

(58) Field of Classification Search
CPC .. A61H 31/007; A61H 31/004; A61H 31/005; A61H 31/006; A61H 31/02;
(Continued)

(56) References Cited

U.S. PATENT DOCUMENTS

| | | |
|---|---|---|
| 1,848,232 A | 3/1932 | Swope et al. |
| 2,325,049 A | 7/1943 | Frye et al. |

(Continued)

FOREIGN PATENT DOCUMENTS

| | | |
|---|---|---|
| AU | 1487792 B | 10/1992 |
| AU | 60539 B | 11/1994 |

(Continued)

OTHER PUBLICATIONS

US 5,584,866 A, 12/1996, Kroll et al. (withdrawn)
(Continued)

*Primary Examiner* — Steven O Douglas
(74) *Attorney, Agent, or Firm* — The Webb Law Firm

(57) ABSTRACT

A system includes a guidance device that provides feedback to a user to compress a patient's chest at a rate of between about 90 and 110 compressions per minute and at a depth of between about 4.5 centimeters to about 6 centimeters. The system includes a pressure regulation system having a pressure-responsive valve that is configured to be coupled to a patient's airway. The pressure-responsive valve is configured to remain closed during successive chest compressions in order to permit removal at least about 200 ml from the lungs in order to lower intracranial pressure to improve survival with favorable neurological function. The pressure-responsive valve is configured to remain closed until the negative pressure within the patient's airway reaches about −7 cm $H_2O$, at which time the pressure-responsive valve is configured to open to provide respiratory gases to flow to the lungs through the pressure-responsive valve.

20 Claims, 21 Drawing Sheets

Related U.S. Application Data continuation of application No. 14/522,402, filed on Oct. 23, 2014, now Pat. No. 9,352,111, which is a continuation-in-part of application No. 13/411,230, filed on Mar. 2, 2012, now Pat. No. 8,985,098, which is a continuation-in-part of application No. 11/871,879, filed on Oct. 12, 2007, now Pat. No. 8,151,790.

(60) Provisional application No. 60/912,891, filed on Apr. 19, 2007.

(51) Int. Cl.
  *A61M 16/10* (2006.01)
  *A61M 16/20* (2006.01)
  *A61H 31/02* (2006.01)

(52) U.S. Cl.
  CPC .... *A61M 16/0048* (2013.01); *A61M 16/0084* (2014.02); *A61M 16/10* (2013.01); *A61M 16/208* (2013.01); *A61H 31/006* (2013.01); *A61H 31/02* (2013.01); *A61H 2031/002* (2013.01); *A61H 2201/018* (2013.01); *A61H 2201/0173* (2013.01); *A61H 2201/0184* (2013.01); *A61H 2201/107* (2013.01); *A61H 2201/5061* (2013.01); *A61H 2201/5071* (2013.01); *A61H 2201/5084* (2013.01); *A61H 2205/084* (2013.01); *A61H 2230/04* (2013.01); *A61H 2230/065* (2013.01); *A61H 2230/40* (2013.01); *A61H 2230/65* (2013.01); *A61M 2202/0208* (2013.01); *A61M 2205/583* (2013.01)

(58) Field of Classification Search
  CPC ........ A61H 2031/002; A61H 2201/018; A61H 2201/0173; A61H 2201/0184; A61H 2201/107; A61H 2201/5061; A61H 2201/5071; A61H 2201/5084; A61H 2205/084; A61H 2230/04; A61H 2230/065; A61H 2230/40; A61H 2230/65; A61M 16/0048; A61M 16/0084; A61M 16/10; A61M 16/208; A61M 2202/0208; A61M 2205/583
  See application file for complete search history.

(56) References Cited

U.S. PATENT DOCUMENTS

| | | |
|---|---|---|
| 2,774,346 A | 12/1956 | Halliburton |
| 2,854,982 A | 10/1958 | Pagano |
| 2,904,898 A | 9/1959 | Marsden |
| 3,009,266 A | 11/1961 | Brook |
| 3,049,811 A | 8/1962 | Ruben |
| 3,068,590 A | 12/1962 | Padellford |
| 3,077,884 A | 2/1963 | Batrow et al. |
| 3,191,596 A | 6/1965 | Bird et al. |
| 3,199,225 A | 8/1965 | Robertson et al. |
| 3,209,469 A | 10/1965 | James |
| 3,216,413 A | 11/1965 | Arecheta Mota |
| 3,274,705 A | 9/1966 | Breakspear |
| 3,276,147 A | 10/1966 | Padellford |
| 3,307,541 A | 3/1967 | Hewson |
| 3,357,426 A | 12/1967 | Cohen |
| 3,420,232 A | 1/1969 | Bickford |
| 3,459,216 A | 8/1969 | Bloom et al. |
| 3,467,092 A | 9/1969 | Bird et al. |
| 3,509,899 A | 5/1970 | Hewson |
| 3,515,163 A | 6/1970 | Freeman |
| 3,523,529 A | 8/1970 | Kissen |
| 3,552,390 A | 1/1971 | Muller |
| 3,562,924 A | 2/1971 | Baerman et al. |
| 3,562,925 A | 2/1971 | Baermann et al. |
| 3,568,333 A | 3/1971 | Clark |
| 3,662,751 A | 5/1972 | Barkalow et al. |
| 3,669,108 A | 6/1972 | Sundblom et al. |
| 3,734,100 A | 5/1973 | Walker et al. |
| 3,739,776 A | 6/1973 | Bird et al. |
| 3,794,043 A | 2/1974 | McGinnis |
| 3,815,606 A | 6/1974 | Mazal |
| 3,834,383 A | 9/1974 | Weigl et al. |
| 3,872,609 A | 3/1975 | Smrcka |
| 3,874,093 A | 4/1975 | Garbe |
| 3,875,626 A | 4/1975 | Tysk et al. |
| 3,933,171 A | 1/1976 | Hay |
| 3,949,388 A | 4/1976 | Fuller |
| 3,973,564 A | 8/1976 | Carden |
| 3,981,398 A | 9/1976 | Boshoff |
| 3,993,059 A | 11/1976 | Sjostrand |
| 4,037,595 A | 7/1977 | Elam |
| 4,041,943 A | 8/1977 | Miller |
| 4,054,134 A | 10/1977 | Kritzer |
| 4,077,400 A | 3/1978 | Harrigan |
| 4,077,404 A | 3/1978 | Elam |
| 4,095,590 A | 6/1978 | Harrigan |
| 4,166,458 A | 9/1979 | Harrigan |
| 4,193,406 A | 3/1980 | Jinotti |
| 4,198,963 A | 4/1980 | Barkalow et al. |
| 4,226,233 A | 10/1980 | Kritzer |
| 4,237,872 A | 12/1980 | Harrigan |
| 4,240,419 A | 12/1980 | Furlong et al. |
| 4,259,951 A | 4/1981 | Chernack et al. |
| 4,262,667 A | 4/1981 | Grant |
| 4,297,999 A | 11/1981 | Kitrell |
| 4,298,023 A | 11/1981 | McGinnis |
| 4,316,458 A | 2/1982 | Hammerton-Fraser |
| 4,320,754 A | 3/1982 | Watson et al. |
| 4,326,507 A | 4/1982 | Barkalow |
| 4,331,426 A | 5/1982 | Sweeney |
| 4,349,015 A | 9/1982 | Alferness |
| 4,360,345 A | 11/1982 | Hon |
| 4,397,306 A | 8/1983 | Weisfeldt et al. |
| 4,424,806 A | 1/1984 | Newman et al. |
| 4,446,864 A | 5/1984 | Watson et al. |
| 4,448,192 A | 5/1984 | Stawitcke et al. |
| 4,449,526 A | 5/1984 | Elam |
| 4,481,938 A | 11/1984 | Lindley |
| 4,501,582 A | 2/1985 | Schulz |
| 4,513,737 A | 4/1985 | Mabuchi |
| 4,519,388 A | 5/1985 | Schwanbom et al. |
| 4,520,811 A | 6/1985 | White et al. |
| 4,533,137 A | 8/1985 | Sonne |
| 4,543,951 A | 10/1985 | Phuc |
| 4,588,383 A | 5/1986 | Parker et al. |
| 4,598,706 A | 7/1986 | Darowski et al. |
| 4,601,465 A | 7/1986 | Roy |
| 4,602,653 A | 7/1986 | Ruiz-Vela et al. |
| 4,637,386 A | 1/1987 | Baum |
| 4,738,249 A | 4/1988 | Linman et al. |
| 4,750,493 A | 6/1988 | Brader |
| 4,774,941 A | 10/1988 | Brader |
| 4,797,104 A | 1/1989 | Laerdal et al. |
| 4,807,638 A | 2/1989 | Sramek |
| 4,809,683 A | 3/1989 | Hanson |
| 4,827,935 A | 5/1989 | Geddes et al. |
| 4,828,501 A | 5/1989 | Ingenito et al. |
| 4,863,385 A | 9/1989 | Pierce |
| 4,881,527 A | 11/1989 | Lerman |
| 4,898,166 A | 2/1990 | Rose et al. |
| 4,898,167 A | 2/1990 | Pierce et al. |
| 4,928,674 A | 5/1990 | Halperin et al. |
| 4,932,879 A | 6/1990 | Ingenito et al. |
| 4,971,042 A | 11/1990 | Lerman |
| 4,971,051 A | 11/1990 | Toffolon |
| 4,984,987 A | 1/1991 | Brault et al. |
| 5,014,698 A | 5/1991 | Cohen |
| 5,016,627 A | 5/1991 | Dahrendorf et al. |
| 5,029,580 A | 7/1991 | Radford et al. |
| 5,042,500 A | 8/1991 | Norlien et al. |
| 5,050,593 A | 9/1991 | Poon |
| 5,056,505 A | 10/1991 | Warwick et al. |
| 5,083,559 A | 1/1992 | Brault et al. |

(56) References Cited

U.S. PATENT DOCUMENTS

| | | | |
|---|---|---|---|
| 5,109,840 | A | 5/1992 | Daleiden |
| 5,119,825 | A | 6/1992 | Huhn |
| 5,150,291 | A | 9/1992 | Cummings et al. |
| 5,163,424 | A | 11/1992 | Kohnke |
| 5,183,038 | A | 2/1993 | Hoffman et al. |
| 5,184,620 | A | 2/1993 | Cudahy et al. |
| 5,188,098 | A | 2/1993 | Hoffman et al. |
| 5,193,529 | A | 3/1993 | Labaere |
| 5,193,544 | A | 3/1993 | Jaffe |
| 5,195,896 | A | 3/1993 | Sweeney et al. |
| 5,217,006 | A | 6/1993 | McCulloch |
| 5,231,086 | A | 7/1993 | Sollevi |
| 5,235,970 | A | 8/1993 | Augustine |
| 5,238,409 | A | 8/1993 | Brault et al. |
| 5,239,988 | A | 8/1993 | Swanson et al. |
| 5,263,476 | A | 11/1993 | Henson |
| 5,265,595 | A | 11/1993 | Rudolph |
| 5,282,463 | A | 2/1994 | Hammersley |
| 5,295,481 | A | 3/1994 | Geeham |
| 5,301,667 | A | 4/1994 | McGrail et al. |
| 5,305,743 | A | 4/1994 | Brain |
| 5,306,293 | A | 4/1994 | Zacouto |
| 5,312,259 | A | 5/1994 | Flynn |
| 5,313,938 | A | 5/1994 | Garfield et al. |
| 5,316,907 | A | 5/1994 | Lurie et al. |
| 5,330,514 | A | 7/1994 | Egelandsdal et al. |
| 5,335,654 | A | 8/1994 | Rapoport |
| 5,353,788 | A | 10/1994 | Miles |
| 5,355,879 | A | 10/1994 | Brain |
| 5,359,998 | A | 11/1994 | Lloyd |
| 5,366,231 | A | 11/1994 | Hung |
| 5,377,671 | A | 1/1995 | Biondi et al. |
| 5,383,786 | A | 1/1995 | Kohnke |
| 5,388,575 | A | 2/1995 | Taube |
| 5,392,774 | A | 2/1995 | Sato |
| 5,395,399 | A | 3/1995 | Rosenwald |
| 5,397,237 | A | 3/1995 | Dhont et al. |
| 5,398,714 | A | 3/1995 | Price |
| 5,413,110 | A | 5/1995 | Cummings et al. |
| 5,423,685 | A | 6/1995 | Adamson et al. |
| 5,423,772 | A | 6/1995 | Lurie et al. |
| 5,425,742 | A | 6/1995 | Joy |
| 5,437,272 | A | 8/1995 | Fuhrman |
| 5,452,715 | A | 9/1995 | Boussignac |
| 5,454,779 | A | 10/1995 | Lurie et al. |
| 5,458,562 | A | 10/1995 | Cooper |
| 5,468,151 | A | 11/1995 | Egelandsdal et al. |
| 5,474,533 | A | 12/1995 | Ward et al. |
| 5,477,860 | A | 12/1995 | Essen-Moller |
| 5,490,820 | A | 2/1996 | Schock et al. |
| 5,492,115 | A | 2/1996 | Abramov et al. |
| 5,492,116 | A | 2/1996 | Scarberry et al. |
| 5,496,257 | A | 3/1996 | Kelly |
| 5,507,282 | A | 4/1996 | Younes |
| 5,517,986 | A | 5/1996 | Starr et al. |
| 5,544,648 | A | 8/1996 | Fischer, Jr. |
| 5,549,106 | A | 8/1996 | Gruenke et al. |
| 5,549,581 | A | 8/1996 | Lurie et al. |
| 5,551,420 | A | 9/1996 | Lurie et al. |
| 5,557,049 | A | 9/1996 | Ratner |
| 5,580,255 | A | 12/1996 | Flynn |
| 5,582,182 | A | 12/1996 | Hillsman |
| 5,588,422 | A | 12/1996 | Lurie et al. |
| 5,593,306 | A | 1/1997 | Kohnke |
| 5,606,968 | A | 3/1997 | Mang |
| 5,614,490 | A | 3/1997 | Przybelski |
| 5,617,844 | A | 4/1997 | King |
| 5,618,665 | A | 4/1997 | Lurie et al. |
| 5,619,665 | A | 4/1997 | Emma |
| 5,628,305 | A | 5/1997 | Melker |
| 5,632,298 | A | 5/1997 | Artinian |
| 5,643,231 | A | 7/1997 | Lurie et al. |
| 5,645,522 | A | 7/1997 | Lurie et al. |
| 5,657,751 | A | 8/1997 | Karr, Jr. |
| 5,678,535 | A | 10/1997 | DiMarco |
| 5,685,298 | A | 11/1997 | Idris |
| 5,692,498 | A | 12/1997 | Lurie et al. |
| 5,697,364 | A | 12/1997 | Chua et al. |
| 5,701,883 | A | 12/1997 | Hete et al. |
| 5,701,889 | A | 12/1997 | Danon |
| 5,704,346 | A | 1/1998 | Inoue |
| 5,720,282 | A | 2/1998 | Wright |
| 5,722,963 | A | 3/1998 | Lurie et al. |
| 5,730,122 | A | 3/1998 | Lurie |
| 5,735,876 | A | 4/1998 | Kroll et al. |
| 5,738,637 | A | 4/1998 | Kelly et al. |
| 5,743,864 | A | 4/1998 | Baldwin, II |
| 5,782,883 | A | 7/1998 | Kroll et al. |
| 5,794,615 | A | 8/1998 | Estes |
| 5,806,512 | A | 9/1998 | Abramov et al. |
| 5,814,086 | A | 9/1998 | Hirschberg et al. |
| 5,817,997 | A | 10/1998 | Wernig |
| 5,823,185 | A | 10/1998 | Chang |
| 5,823,787 | A | 10/1998 | Gonzalez et al. |
| 5,827,893 | A | 10/1998 | Lurie et al. |
| 5,832,920 | A | 11/1998 | Field |
| 5,853,292 | A * | 12/1998 | Eggert .................. G09B 23/28 434/262 |
| 5,881,725 | A | 3/1999 | Hoffman et al. |
| 5,885,084 | A | 3/1999 | Pastrick et al. |
| 5,891,062 | A | 4/1999 | Schock et al. |
| 5,896,857 | A | 4/1999 | Hely et al. |
| 5,916,165 | A | 6/1999 | Duchon et al. |
| 5,919,210 | A | 7/1999 | Lurie et al. |
| 5,927,273 | A | 7/1999 | Federowicz et al. |
| 5,937,853 | A | 8/1999 | Strom |
| 5,941,710 | A | 8/1999 | Lampotang et al. |
| 5,975,081 | A | 11/1999 | Hood et al. |
| 5,977,091 | A | 11/1999 | Nieman et al. |
| 5,984,909 | A | 11/1999 | Lurie et al. |
| 5,988,166 | A | 11/1999 | Hayek |
| 6,001,085 | A | 12/1999 | Lurie et al. |
| 6,010,470 | A | 1/2000 | Albery et al. |
| 6,029,667 | A | 2/2000 | Lurie |
| 6,042,532 | A | 3/2000 | Freed et al. |
| 6,062,219 | A | 5/2000 | Lurie et al. |
| 6,078,834 | A | 6/2000 | Lurie et al. |
| 6,086,582 | A | 7/2000 | Altman et al. |
| 6,123,074 | A | 9/2000 | Hete et al. |
| 6,131,571 | A | 10/2000 | Lampotang et al. |
| 6,155,257 | A | 12/2000 | Lurie et al. |
| 6,155,647 | A | 12/2000 | Albecker, III |
| 6,165,105 | A | 12/2000 | Boutellier et al. |
| 6,167,879 | B1 | 1/2001 | Sievers et al. |
| 6,174,295 | B1 | 1/2001 | Cantrell et al. |
| 6,176,237 | B1 | 1/2001 | Wunderlich et al. |
| 6,193,519 | B1 | 2/2001 | Eggert et al. |
| 6,209,540 | B1 | 4/2001 | Sugiura et al. |
| 6,224,562 | B1 | 5/2001 | Lurie et al. |
| 6,234,916 | B1 | 5/2001 | Carusillo et al. |
| 6,234,985 | B1 | 5/2001 | Lurie et al. |
| 6,277,107 | B1 | 8/2001 | Lurie et al. |
| 6,296,490 | B1 | 10/2001 | Bowden |
| 6,312,399 | B1 | 11/2001 | Lurie et al. |
| 6,334,441 | B1 | 1/2002 | Zowtiak et al. |
| 6,356,785 | B1 | 3/2002 | Snyder et al. |
| 6,369,114 | B1 | 4/2002 | Weil et al. |
| 6,374,827 | B1 | 4/2002 | Bowden et al. |
| 6,390,996 | B1 | 5/2002 | Halperin et al. |
| 6,425,393 | B1 | 7/2002 | Lurie et al. |
| 6,439,228 | B1 | 8/2002 | Hete et al. |
| 6,459,933 | B1 | 10/2002 | Lurie et al. |
| 6,463,327 | B1 | 10/2002 | Lurie et al. |
| 6,486,206 | B1 | 11/2002 | Lurie |
| 6,526,970 | B2 | 3/2003 | DeVries et al. |
| 6,526,973 | B1 | 3/2003 | Lurie et al. |
| 6,536,432 | B2 | 3/2003 | Truschel |
| 6,544,172 | B2 | 4/2003 | Toeppen-Sprigg |
| 6,555,057 | B1 | 4/2003 | Barbut et al. |
| 6,578,574 | B1 | 6/2003 | Kohnke |
| 6,584,973 | B1 | 7/2003 | Biondi et al. |
| 6,587,726 | B2 | 7/2003 | Lurie et al. |
| 6,595,213 | B2 | 7/2003 | Bennarsten |
| 6,604,523 | B2 | 8/2003 | Lurie et al. |

(56) References Cited

U.S. PATENT DOCUMENTS

| | | | |
|---|---|---|---|
| 6,622,274 B1 | 9/2003 | Lee et al. |
| 6,622,724 B1 | 9/2003 | Truitt et al. |
| 6,631,716 B1 | 10/2003 | Robinson et al. |
| 6,656,166 B2 | 12/2003 | Lurie et al. |
| 6,662,032 B1 | 12/2003 | Gavish et al. |
| 6,676,613 B2 | 1/2004 | Cantrell et al. |
| 6,726,634 B2 | 4/2004 | Freeman |
| 6,729,334 B1 | 5/2004 | Baran |
| 6,758,217 B1 | 7/2004 | Younes |
| 6,776,156 B2 | 8/2004 | Lurie et al. |
| 6,780,017 B2 | 8/2004 | Pastrick et al. |
| 6,792,947 B1 | 9/2004 | Bowden |
| 6,863,656 B2 | 3/2005 | Lurie |
| 6,877,511 B2 | 4/2005 | DeVries et al. |
| 6,935,336 B2 | 8/2005 | Lurie et al. |
| 6,938,618 B2 | 9/2005 | Lurie et al. |
| 6,951,546 B2 * | 10/2005 | Palmer ..................... A61F 5/03 601/152 |
| 6,986,349 B2 | 1/2006 | Lurie |
| 6,988,499 B2 | 1/2006 | Holt et al. |
| 7,011,622 B2 | 3/2006 | Kuyava et al. |
| 7,032,596 B2 | 4/2006 | Thompson et al. |
| 7,044,128 B2 | 5/2006 | Lurie et al. |
| 7,066,173 B2 | 6/2006 | Banner et al. |
| 7,082,945 B2 | 8/2006 | Lurie |
| 7,096,866 B2 | 8/2006 | Be'eri et al. |
| 7,174,891 B2 | 2/2007 | Lurie et al. |
| 7,185,649 B2 | 3/2007 | Lurie |
| 7,188,622 B2 | 3/2007 | Martin et al. |
| 7,195,012 B2 | 3/2007 | Lurie |
| 7,195,013 B2 | 3/2007 | Lurie |
| 7,204,251 B2 | 4/2007 | Lurie |
| 7,210,480 B2 | 5/2007 | Lurie et al. |
| 7,220,235 B2 | 5/2007 | Geheb et al. |
| 7,226,427 B2 | 6/2007 | Steen |
| 7,275,542 B2 | 10/2007 | Lurie et al. |
| 7,311,668 B2 | 12/2007 | Lurie |
| 7,469,700 B2 | 12/2008 | Baran |
| 7,487,773 B2 | 2/2009 | Li |
| 7,500,481 B2 | 3/2009 | Delache et al. |
| 7,594,508 B2 | 9/2009 | Doyle |
| 7,650,181 B2 | 1/2010 | Freeman et al. |
| 7,682,312 B2 | 3/2010 | Lurie |
| 7,766,011 B2 | 8/2010 | Lurie |
| 7,793,659 B2 | 9/2010 | Breen |
| 7,824,436 B2 | 11/2010 | Barbut et al. |
| 7,836,881 B2 | 11/2010 | Lurie et al. |
| 7,899,526 B2 | 3/2011 | Benditt et al. |
| 8,011,367 B2 | 9/2011 | Lurie et al. |
| 8,108,204 B2 | 1/2012 | Gabrilovich et al. |
| 8,151,790 B2 | 4/2012 | Lurie et al. |
| 8,210,176 B2 | 7/2012 | Metzger et al. |
| 8,287,474 B1 | 10/2012 | Koenig et al. |
| 8,388,682 B2 | 3/2013 | Hendricksen et al. |
| 8,408,204 B2 | 4/2013 | Lurie |
| 8,702,633 B2 | 4/2014 | Voss et al. |
| 8,755,902 B2 | 6/2014 | Lurie et al. |
| 8,939,922 B2 | 1/2015 | Strand et al. |
| 9,238,115 B2 | 1/2016 | Marshall et al. |
| 2001/0003984 A1 | 6/2001 | Bennarsten et al. |
| 2001/0029339 A1 | 10/2001 | Orr et al. |
| 2001/0047140 A1 | 11/2001 | Freeman |
| 2002/0007832 A1 | 1/2002 | Doherty |
| 2002/0069878 A1 | 6/2002 | Lurie et al. |
| 2002/0104544 A1 | 8/2002 | Ogushi et al. |
| 2002/0170562 A1 | 11/2002 | Lurie et al. |
| 2002/0179090 A1 | 12/2002 | Boussignac |
| 2003/0000526 A1 | 1/2003 | Gobel |
| 2003/0037784 A1 | 2/2003 | Lurie |
| 2003/0062040 A1 | 4/2003 | Lurie et al. |
| 2003/0062041 A1 | 4/2003 | Keith et al. |
| 2003/0192547 A1 | 10/2003 | Lurie et al. |
| 2004/0016428 A9 | 1/2004 | Lurie |
| 2004/0058305 A1 | 3/2004 | Lurie et al. |
| 2004/0200473 A1 | 10/2004 | Lurie et al. |
| 2004/0200474 A1 | 10/2004 | Lurie |
| 2004/0210281 A1 | 10/2004 | Dzeng et al. |
| 2004/0211415 A1 | 10/2004 | Lurie |
| 2004/0211416 A1 | 10/2004 | Lurie |
| 2004/0211417 A1 | 10/2004 | Lurie |
| 2004/0231664 A1 | 11/2004 | Lurie et al. |
| 2004/0267325 A1 | 12/2004 | Geheb et al. |
| 2005/0016534 A1 | 1/2005 | Ost |
| 2005/0075531 A1 | 4/2005 | Loeb et al. |
| 2005/0126567 A1 | 6/2005 | Lurie |
| 2005/0165334 A1 | 7/2005 | Lurie |
| 2005/0199237 A1 | 9/2005 | Lurie |
| 2005/0217677 A1 | 10/2005 | Lurie et al. |
| 2005/0267381 A1 | 12/2005 | Benditt et al. |
| 2006/0089574 A1 | 4/2006 | Paradis |
| 2006/0129191 A1 | 6/2006 | Sullivan et al. |
| 2006/0270952 A1 | 11/2006 | Freeman et al. |
| 2007/0017523 A1 | 1/2007 | Be-Eri et al. |
| 2007/0021683 A1 | 1/2007 | Benditt et al. |
| 2007/0060785 A1 | 3/2007 | Freeman et al. |
| 2007/0199566 A1 | 8/2007 | Be'eri |
| 2007/0221222 A1 | 9/2007 | Lurie |
| 2007/0277826 A1 | 12/2007 | Lurie |
| 2008/0039748 A1 | 2/2008 | Palmer et al. |
| 2008/0047555 A1 | 2/2008 | Lurie et al. |
| 2008/0092891 A1 | 4/2008 | Cewers |
| 2008/0097258 A1 | 4/2008 | Walker |
| 2008/0097385 A1 | 4/2008 | Vinten-Johansen et al. |
| 2008/0108905 A1 | 5/2008 | Lurie |
| 2008/0255482 A1 | 10/2008 | Lurie |
| 2008/0257344 A1 | 10/2008 | Lurie et al. |
| 2009/0020128 A1 | 1/2009 | Metzger et al. |
| 2009/0062701 A1 | 3/2009 | Yannopoulos et al. |
| 2009/0076573 A1 | 3/2009 | Burnett et al. |
| 2009/0164000 A1 | 6/2009 | Shirley |
| 2009/0277447 A1 | 11/2009 | Voss et al. |
| 2009/0299156 A1 | 12/2009 | Simpson et al. |
| 2010/0000535 A1 | 1/2010 | Wickham et al. |
| 2010/0147302 A1 | 6/2010 | Selvarajan et al. |
| 2010/0174278 A1 | 7/2010 | Barbut et al. |
| 2010/0179442 A1 | 7/2010 | Lurie |
| 2010/0247682 A1 | 9/2010 | Gladwin et al. |
| 2010/0319691 A1 | 12/2010 | Lurie et al. |
| 2011/0056491 A1 | 3/2011 | Rumph et al. |
| 2011/0098612 A1 | 4/2011 | Lurie |
| 2011/0160782 A1 | 6/2011 | Lurie et al. |
| 2011/0201979 A1 | 8/2011 | Voss et al. |
| 2011/0297147 A1 | 12/2011 | Lick et al. |
| 2012/0016279 A1 | 1/2012 | Banville et al. |
| 2012/0203147 A1 | 8/2012 | Lurie et al. |
| 2012/0302908 A1 | 11/2012 | Hemnes et al. |
| 2012/0330199 A1 | 12/2012 | Lurie et al. |
| 2012/0330200 A1 | 12/2012 | Voss et al. |
| 2013/0118498 A1 | 5/2013 | Robitaille et al. |
| 2013/0172768 A1 | 7/2013 | Lehman |
| 2013/0231593 A1 | 9/2013 | Yannopoulos et al. |
| 2013/0269701 A1 | 10/2013 | Lurie |
| 2014/0005566 A1 | 1/2014 | Homuth et al. |
| 2014/0048061 A1 | 2/2014 | Yannopoulos et al. |
| 2016/0287834 A1 | 10/2016 | Bennett |

FOREIGN PATENT DOCUMENTS

| | | |
|---|---|---|
| AU | 687942 B | 5/1995 |
| CA | 668771 A | 8/1963 |
| CA | 2077608 A1 | 3/1993 |
| CA | 2214887 A1 | 9/1996 |
| CN | 1183731 A | 6/1998 |
| DE | 2453490 A1 | 5/1975 |
| DE | 4308493 A1 | 9/1994 |
| EP | 0029352 A1 | 5/1981 |
| EP | 0139363 A1 | 5/1985 |
| EP | 0245142 A1 | 11/1987 |
| EP | 0367285 A2 | 5/1990 |
| EP | 0411714 A1 | 2/1991 |
| EP | 0509773 A1 | 10/1992 |
| EP | 0560440 A1 | 9/1993 |
| EP | 0623033 A1 | 11/1994 |
| GB | 1344862 A | 1/1974 |

(56) References Cited

FOREIGN PATENT DOCUMENTS

| | | |
|---|---|---|
| GB | 1465127 A | 2/1977 |
| GB | 2117250 A | 10/1983 |
| GB | 2139099 A | 11/1984 |
| JP | 2005000675 A | 1/2005 |
| JP | 2006524543 A | 11/2006 |
| JP | 2007504859 A | 3/2007 |
| WO | 9005518 A1 | 5/1990 |
| WO | 9302439 A1 | 2/1993 |
| WO | 9321982 A1 | 11/1993 |
| WO | 9426229 A1 | 11/1994 |
| WO | 9513108 A1 | 5/1995 |
| WO | 9528193 A1 | 10/1995 |
| WO | 9628215 A1 | 9/1996 |
| WO | 9820938 A1 | 5/1998 |
| WO | 9947197 A1 | 9/1999 |
| WO | 9963926 A2 | 12/1999 |
| WO | 0020061 A1 | 4/2000 |
| WO | 0102049 A2 | 1/2001 |
| WO | 0170092 A2 | 9/2001 |
| WO | 0170332 A2 | 9/2001 |
| WO | 02092169 A1 | 11/2002 |
| WO | 2004096109 A3 | 11/2004 |
| WO | 2006088373 A1 | 8/2006 |
| WO | 2008147229 A1 | 12/2008 |
| WO | 2010044034 A1 | 4/2010 |
| WO | 2013064888 A1 | 5/2013 |
| WO | 2013096495 A1 | 6/2013 |
| WO | 2014026193 A1 | 2/2014 |

OTHER PUBLICATIONS

Advanced Circulatory Systems, Inc. (Jan. 2014), Emerging Data: The Resuscitation Outcomes Consortium (ROC) PRIMED Study on the Efficacy of the ITD (#49-0864-000,06) [Brochure], Roseville, MN:Advanced Circulatory Systems, Inc. 2 pages.
Advanced Circulatory Systems, Inc. (Jan. 2013), Emerging Data: The Resuscitation Outcomes Consortium (ROC) Primed Study on the Efficacy of the ITD (#49-0864-000,05) [Brochure], Roseville, MN:Advanced Circulatory Systems, Inc. 2 pages.
Advanced Circulatory Systems, Inc. (Mar. 2012), Benefits of the ResQPOD Based Upon the ROC PRIMED Study (#49-0864-000,04) [Brochure], Roseville, MN:Advanced Circulatory Systems, Inc. 2 pages.
Advanced Circulatory Systems, Inc. (Jan. 2012), Benefits of the ResQPOD Based Upon the ROC PRIMED Study (#49-0864-000,03) [Brochure], Roseville, MN:Advanced Circulatory Systems, Inc. 2 pages.
Advanced Circulatory Systems, Inc. (Aug. 2011),Early Intervention is Life-Saving in Cardiac Arrest (#49-0864-000,01) [Brochure], Roseville, MN:Advanced Circulatory Systems, Inc. 2 pages.
Advanced Circulatory Systems, Inc. (Aug. 2011),Early Intervention is Life-Saving in Cardiac Arrest (#49-0864-000,02) [Brochure], Roseville, MN:Advanced Circulatory Systems, Inc. 2 pages.
Advanced Circulatory Systems, Inc. (2013), ResQPOD More than a Heartbeat (#49-0336-000,08) [Brochure], Roseville, MN:Advanced Circulatory Systems, Inc. 2 pages.
Advanced Circulatory Systems, Inc. (2011), ResQPOD ITD:Strengthening the Chain of Survival (#49-0336000,06) [Brochure], Roseville, MN:Advanced Circulatory Systems, Inc. 2 pages.
Advanced Circulatory Systems, Inc. (2010), ResQPOD Impedance Threshold Device:Strengthening the Chain of Survival (#49-0336000,05) [Brochure], Roseville, MN:Advanced Circulatory Systems, Inc. 2 pages.
Advanced Circulatory Systems, Inc. (2010), ResQPOD Impedance Threshold Device:Strengthening the Chain of Survival (#49-0336000,04) [Brochure], Roseville, MN:Advanced Circulatory Systems, Inc. 2 pages.
Advanced Circulatory Systems, Inc. (2010), ResQPOD Impedance Threshold Device 10.0: Strengthening the Chain of Survival (#49-0336000,03) [Brochure], Roseville, MN:Advanced Circulatory Systems, Inc. 2 pages.
Advanced Circulatory Systems, Inc. (2006). ResQPOD® Circulatory Enhancer: Strengthening the Chain of Survival [#49-0336-000, 02). [Brochure]. Roseville.MN: Advanced Circulatory Systems,Inc., 2 pages.
Advanced Circulatory Systems, Inc. (2006). ResQPOD® Circulatory Enhancer: Strengthening the Chain of Survival [#49-0336-000, 01) [Brochure). Roseville, MN: Advanced Circulatory Systems, Inc. 2 pages.
Advanced Circulatory Systems. Inc. (2011). ResQPOD® Perfusion on Demand: ResQPOD Impedance Threshold Device (#49-0324-001, 05) [Brochure). Roseville, MN: Advanced Circulatory Systems, Inc., 2 pages.
Advanced Circulatory Systems, Inc. (2011). ResQPOD® Perfusion on Demand: ResQPOD Impedance Threshold Device (#49-0324-001, 04) [Brochure). Roseville, MN: Advanced Circulatory Systems, Inc. 2 pages.
Advanced Circulatory Systems,Inc. (2010). ResQPOD® Perfusion on Demand: ResQPOD Impedance Threshold Device (#49-0324-001, 03) [Brochure). Roseville, MN: Advanced Circulatory Systems, Inc., 2 pages.
Advanced Circulatory Systems,Inc. (2009). ResQPOD® Perfusion on Demand: ResQPOD Impedance Threshold Device (#49-0324-001, 02) [Brochure). Roseville, MN: Advanced Circulatory Systems, Inc., 2 pages.
Advanced Circulatory Systems,Inc. (2005). Introducing ResQPOD® (#49-0324-000, 01) [Brochure). Roseville, MN: Advanced Circulatory Systems, Inc., 2 pages.
Ambu InternationaINS Directions for use of Ambu® CardioPump™•Sep. 1992, 8 pages.
Aufderheide et al., "Standard cardiopulmonary resuscitation versus active compression-decompression cardiopulmonary resuscitation with augmentation of negative intrathoracic pressure for out-of-hospital cardiac arrest: A randomized trial," 2011, Lancet, vol. 377, pp. 301-311.
Aufderheide et al., "Hyperventilation-Induced Hypotension During Cardiopulmonary Resuscitation," Circulation; 2004, vol. 109:16, pp. 1960-1965.
Babbs, "CPR Techniques that Combine Chest and Abdominal Compression and Decompression: Hemodynamic Insights from a Spreadsheet Model," Circulation,1999, pp. 2146-2152.
Christenson et al., "Abdominal Compressions During CPR: Hemodynamic Effects of Altering Timing and Force", The Journal of Emergency Medicine, 1992,vol. 10, pp. 257-266.
Cohen et al., "Active compression-decompression resuscitation: A novel method of cardiopulmonary resuscitation," American Heart Journal vol. 124:5, pp. 1145-1150.
Cohen et al., "Active Compression-Decompression: A New Method of Cardiopulmonary Resuscitation," 1992, JAMA, vol. 267:29, pp. 2916-2923.
Dupuis, "Ventilators—Theory and Clinical Application," Jan. 1986, The C.V. Mosby Company, pp. 447-448, 481, 496.
Geddes et al., "Inspiration Produced by Bilateral Electromagnetic, Cervical Phrenic Nerve Stimulation in Man," IEEE Transactions on Biomedical Engineering, 1991, vol. 38:9, pp. 1047-1048.
Geddes et al., "Optimum Stimulus Frequency for Contracting the Inspiratory Muscles with Chest-Surface Electrodes to Produce Artificial respiration," Annals of Biomedical Engineering, 1990, vol. 18, pp. 103-108.
Geddes et al., "Electrically Produced Artificial Ventilation," Medical Instrumentation, 1988, vol. 22:5; pp. 263-271.
Geddes, "Electroventilation—A Missed Opportunity?" Biomedical Instrumentation & Technology, 1998, pp. 401-414.
Glen et al., "Diaphragm Pacing by Electrical Stimulation of the Phrenic Nerve," Neurosurgery, 1985, vol. 17:6, pp. 974-984.
Glenn et al., "Twenty Years of Experience in Phrenic Nerve Stimulation to Pace the Diaphragm," Nov./Dec. 1986, Part I, Pace 9, pp. 780-784.
Guidelines for Cardiopulmonary Resuscitation and Emergency Cardiac Care, JAMA, 1992, vol. 268; pp. 2172-2177.
Kotze et al., "Diaphragm pacing in the treatment of ventilatory failure," SAMT, 1995, vol. 68, pp. 223-224.

(56) References Cited

OTHER PUBLICATIONS

Laghi et al., "Comparison of Magnetic and Electrical Phrenic Nerve Stimulation in assessment of Diaphragmantic Contractility," American Physiological Society, 1996, pp. 1731-1742.
Lindner et al., "Effects of Active Compression-Decompression Resuscitation on Myocardialand Cerebral Blood Flow in Pigs," Circulation, 1993, vol. 88:3, 1254-1263.
Lurie et al., "Comparison of a 10-Breaths-Per-Minute Versus a 2-Breaths-Per-Minute Strategy During Cardiopulmonary Resuscitation in a Porcine Model of Cardiac Arrest," Respiratory Care, 2008, vol. 53:7, pp. 862-870.
Lurie et al., "Regulated to Death: The Matter of Informed Consent for Human Experimentation in Emergency Resuscitation Research," PACE, 1995, vol. 8, pp. 1443-1447.
Michigan Instruments, Inc.Thumper 1007CC Continuous Compression Cardiopulmonary Resuscitation System, obtained online 715/2006 at http://WwW.michiganinstruments.com/resus-thumper.htm, 1 page.
Mushin et al., "Automatic Ventilation of the Lungs—The Lewis-Leigh Inflating Valve," 1969, Blackwell Scientific, Oxford, GB, p. 838.
Schultz et al., "Sodium nitroprusside enhanced cardiopulmonary resuscitation (SNPeCPR) improves vital organ perfusion pressures and carotid blood flow in a porcine model of cardiac arrest," Resuscitation, 2012, vol. 83, pp. 374-377.
Segal et al., "Ischemic postconditioning at the initiation of cardiopulmonary resuscitation facilitates cardiac and cerebral recovery after prolonged untreated ventricular fibrillation," Resuscitation, 2012, pp. 1-7.
Shapiro et al., "Neurosurgical Anesthesia and Intracranial Hypertension," Anesthesia, 3rd Edition, 1990, Church Livingston, New York, Chapter 54.
Yannopoulos et al., "Controlled pauses at the initiation of sodium nitroprussdi e-enhanced cardiopulmonary resuscitation facilitate neurological and cardiac recovery after 15 minutes of untreated ventricular fibrillation," Critical Care Medicine , 2012, vol. 40:5, pp. 1-8.
Yannopoulos et al., "Intrathoracic Pressure Regulator During Continuous-Chest-Compression Advanced Cardiac Resuscitation Improves Vital Organ Perfusion Pressures in a Porcine Modelof Cardiac Arrest", Circulation, 2005, pp. 803-811.
Yannopoulos et al., "Intrathoracic Pressure Regulation Improves 24• Hour Survival in a Porcine Modelof Hypovolemic Shock," Anesthesia & Analgesia, ITPR and Survival in Hypovolemic Shock, 2007, vol. 104:1, pp. 157-162.
Yannopoulos et al.,"Intrathoracic pressure regulation improves vital organ perfusion pressures in normovolemic and hypovolemic pigs," Resuscitation, 2006, vol. 70, pp. 445-453.
Yannopoulos et al., "Sodium nitroprusside enhanced cardiopulmonary resuscitation improves survival with good neurological function in a porcine model of prolonged cardiac arrest," Critical Care Medicine, 2011, vol. 39:6 pp. 1-6.
Zhao et. al., "Inhibation of myocardial injury by ischemic postconditioning during reperfusion: comparison with ischemic preconditioning," AJP Heart Circ Physiol, 2003, vol. 285, pp. H579-H588.
Zoll Autopulse Non-Invasive Cardiac Support Pump, obtained online on 715106 at http://www.zoll.com/product.aspx?id=84,1 page.
U.S. Appl. No. 11/871,879, "Volume Exchanger Valve System and Method to Increase Circulation During CPR", filed Oct. 12, 2007.
U.S. Appl. No. 13/411,230, "CPR Volume Exchanger Valve System with Safety Feature and Methods", filed Mar. 2, 2012.
U.S. Appl. No. 14/522,402, "Systems and Methods to Increase Survival With Favorable Neurological Function After Cardiac Arrest", filed Oct. 23, 2014.
U.S. Appl. No. 14/635,525, "CPR Volume Exchanger Valve System With Safety Feature and Methods", filed Mar. 2, 2015.
U.S. Appl. No. 15/158,738, "Systems and Methods to Increase Survival With Favorable Neurological Function After Cardiac Arrest", filed May 19, 2016.

* cited by examiner

SYSTEMS AND METHODS TO INCREASE SURVIVAL WITH FAVORABLE NEUROLOGICAL FUNCTION AFTER CARDIAC ARREST

CROSS REFERENCES TO RELATED APPLICATIONS

This application is a continuation of co-pending U.S. patent application Ser. No. 15/158,738, filed May 19, 2016, which is a continuation of U.S. patent application Ser. No. 14/522,402, filed Oct. 23, 2014, and issued as U.S. Pat. No. 9,352,111, which is a continuation-in-part of U.S. patent application Ser. No. 13/411,230, filed Mar. 2, 2012, and issued as U.S. Pat. No. 8,985,098, which is a continuation-in-part of U.S. patent application Ser. No. 11/871,879, filed Oct. 12, 2007 and issued as U.S. Pat. No. 8,151,790, which claims the benefit of U.S. Provisional Application No. 60/912,891, filed Apr. 19, 2007, the complete disclosures of which are herein incorporated by reference.

BACKGROUND OF THE INVENTION

This invention relates generally to the field of cardiopulmonary resuscitation, and in particular to techniques to increase circulation when performing CPR. More specifically, the invention relates to systems and methods for increasing survival with favorable neurological function after cardiac arrest.

Despite current methods of CPR most people die after cardiac arrest. One of the major reasons is that blood flow to the heart and brain is very poor with traditional manual closed chest CPR. Greater circulation of blood during CPR will result in improved outcomes.

BRIEF SUMMARY OF THE INVENTION

Embodiments of the present invention provide systems and methods for increasing survival with favorable neurological function after cardiac arrest. In one embodiment, a system to increase survival with favorable neurological function after cardiac arrest includes a guidance device that may be configured to provide user feedback as to whether the chest compressions are being performed at a rate between 80 to 120 compressions per minute (preferably at 90 to 110 compressions per minute) and at a depth of 4.5 cm per compression to about 6 cm per compression. The system may also include a pressure regulation system having a pressure-responsive valve that may be configured to be coupled to a patient's airway. The pressure-responsive valve may be configured to remain closed during successive chest compressions in order to permit removal at least about 3 ml/kg from the lungs in order to lower intracranial pressure and increase cerebral brain flow to improve survival with favorable neurological function. To provide some respiratory gas exchange, the pressure-responsive valve may be configured to remain closed until the negative pressure within the patient's airway reaches about −7 cm $H_2O$, at which time the pressure-responsive valve may be configured to open to provide respiratory gases to flow to the lungs through the pressure-responsive valve. When the pressure-responsive valve opens, it provides resistance to the incoming gas flow at a level of about 7 to about 18 cm $H_2O$ at a flow rate of 20 L/min.

In another embodiment, a method to increase survival with favorable neurological function after cardiac arrest is provided. The method may include providing a valve system having a pressure-responsive valve that may be configured to be coupled to a person's airway. The method may also include providing instructions to reduce blood volume from the brain by compressing the chest at a rate between about 80 to about 120 per minute, and more preferably from about 90 to about 110 per minute, at a depth of about 4.5 to about 6 cm. The method may further include providing a guidance device that may be configured to provide user feedback as to whether the chest compressions are being performed at a rate between about 80 to about 120 per minute, and more preferably between 90 to 110 compressions per minute, and at a depth of 4.5 cm per compression to about 6 cm per compression. The method also may include providing instructions to provide positive pressure ventilation at a rate of 6 to 14 breaths/minute with a tidal volume of between about 400 ml and 700 ml.

In another embodiment, a method to increase survival with favorable neurological function after cardiac arrest is provided. The method may include providing a pressure regulation system comprising a pressure-responsive valve that may be configured to be coupled to a patient's airway. The pressure-responsive valve may be configured to remain closed during successive chest compressions in order to permit removal at least about 200 ml from the lungs in order to lower intracranial pressure to improve survival with favorable neurological function. To provide some level of respiratory gas flow to the lungs, the pressure-responsive valve remains closed during successive chest compressions in order to permit removal at least about 200 ml from the lungs in order to lower intracranial pressure to improve survival with favorable neurological function. Further, the pressure-responsive valve is configured to remain closed until the negative pressure within the patient's airway reaches about −7 cm $H_2O$, at which time the pressure-responsive valve is configured to open to provide respiratory gases to flow to the lungs through the pressure-responsive valve. In some cases, the pressure responsive valve is configured so that when the pressure-responsive valve opens, it provides resistance to the incoming gas flow at a level of about 7 to about 18 cm $H_2O$ at a flow rate of 20 L/min. The method may also include providing instructions to reduce blood volume from the brain by compressing the chest at a rate between about 90 to about 110 per minute at a depth of about 4.5 to about 6 cm. The method may further include providing a guidance device that may be configured to provide user feedback as to whether the chest compressions are being performed at a rate between 90 to 110 compressions per minute and at a depth of 4.5 cm per compression to about 6 cm per compression.

DETAILED DESCRIPTION OF THE INVENTION

Figure 1:
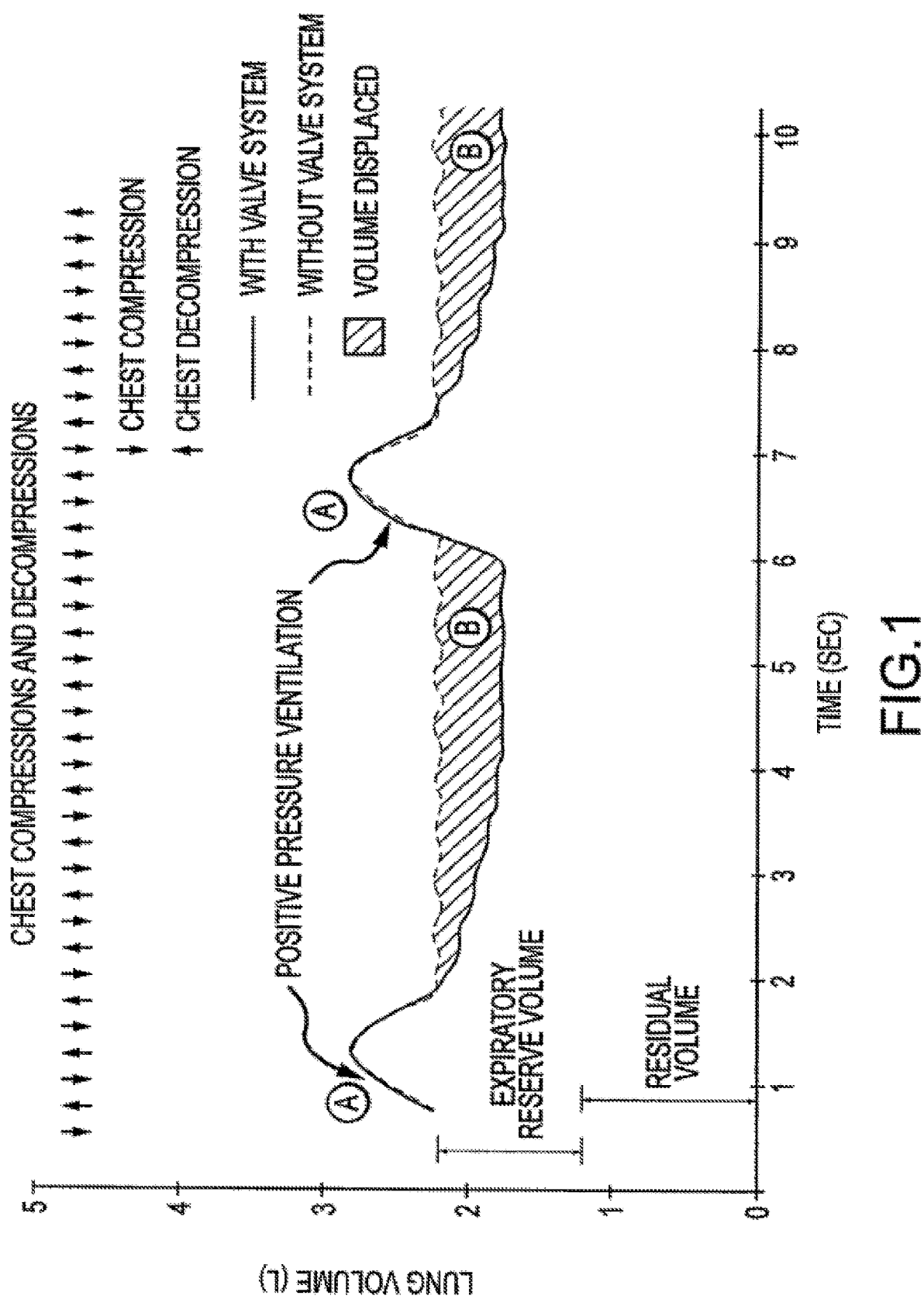
FIG. 1 is a graph illustrating lung volume while performing CPR when applying techniques according to the invention.

Multiple methods of chest compression may be used when performing CPR in patients in cardiac arrest. In this life-threatening situation, the heart is not capable of circulating blood so non-invasive external means are used to assist in the circulation of blood to the vital organs including the heart, lungs, and brain. The methods and devices that may be used to circulate blood during cardiac arrest include manual closed chest CPR, active compression decompression (ACD) CPR where the patient's chest is actively pulled upward (including by use of a mechanical assistance device that is adhered to the chest) to achieve complete chest wall recoil, mechanical CPR with manual or automated devices that compress the chest and either allow the chest to recoil passively or actively, and devices that compress the chest wall and then function like an iron lung and actively expand the thoracic cage. Some of these approaches and devices only compress the anterior aspect of the chest such as the sternum while other approaches and devices compress all or part of the thorax circumferentially. Some approaches and devices also compress the thorax and abdomen in an alternating sequence. Some approaches also involve compressing the lower extremities to enhance venous blood flow back to the heart and augment arterial pressure so that more blood goes to the brain. Some approaches also involve compressing the back, with the patient lying on his/her stomach. Some devices include both non-invasive methods and devices outlined above that are coupled with invasive devices, such as an intra-aortic balloon, and devices to simultaneously cool the patient Because the cardiac valves remain essentially intact during CPR, blood is pushed out of the heart into the aorta during the chest compression phase of CPR. When the chest wall recoils, blood from extrathoracic compartments (e.g. the abdomen, upper limbs, and head) enters the thorax, specifically the heart and lungs. Without the next chest compression, the blood would pool in the heart and lungs during cardiac arrest as there is insufficient intrinsic cardiac pump activity to promote forward blood flow. Thus, chest compressions are an essential part of CPR.

During the compression phase of standard manual closed chest CPR, air is pushed out of the thorax and into the atmosphere via the trachea and airways. During the decompression phase it passively returns back into the thorax via the same airway system. As such, respiratory gases move out of and back into the thorax. With each compression the pressure within the chest is nearly instantaneously transmitted to the heart and also to the brain via the spinal column and via vascular connections. Thus, with each external chest compression pressure in the thorax and within all of the organs in the thorax is increased. Application of the methods and devices described in this application, in conjunction with any of the methods of CPR noted above, result in less and less air in the thorax, making room for more and more blood to return to the heart during the chest wall recoil phase. This increases circulation to the coronary arteries and lowers intracranial pressure during the chest wall decompression phase and with each subsequent compression increases blood flow to the vital organs, especially the brain. Since the delivery of oxygen is an important aspect of CPR, periodically a positive pressure ventilation needs to be delivered to inflate the lungs and provide oxygen. For example, a positive pressure ventilation device may be used that is configured to supply respiratory gases to the lungs at a rate in the range of about 6 to about 14 breaths/minute with a tidal volume of at least about 600 ml. The lungs can also be inflated by periodic negative pressure ventilation with, for example, an iron lung or chest cuirass device. With both positive and negative pressure ventilation, typically a patient receives a tidal volume of about 500-1000 cc during each active ventilation (positive pressure ventilation). Thus, with the practice of this invention, an equal volume of respiratory gas is extruded from lungs over the course of several compressions so that after about 2 to 6 compressions the delivered volume has been removed from the thorax and its space can be replaced by blood that refills the thoracic space. This exchange is made possible by the fact that pressures within the thorax are transduced from one organ to another nearly instantaneously. This pressure transfer occurs between different thoracic compartments, for example the lungs and the right heart, very rapidly, especially between organs in the thorax with a high degree of compliance. For example, positive pressures are transferred during the compression phase from the lungs to the right heart, and as such right heart pressures are markedly increased with each chest compression. The increase in pressure within the lungs is transferred to the heart, propelling blood within the heart chambers in a forward direction along the course from right atrium to right ventricle to pulmonary artery pulmonary vein, left ventricle, and out the aorta. The inverse is also true, with chest wall recoil the negative pressures are transmitted throughout the thorax, including the spinal cord. This pulls blood into the heart and lungs from outside the thorax. The decreases in pressures within the thorax are augmented by the methods and devices described herein. The more gas that is pushed out of the lungs with each compression and not allowed back in, the more space is made available for blood to flow into the organs within the thorax each time the chest wall recoils. The volume of respiratory gas that is expelled over a series of chest compression/recoil cycles may be about 5 to about 15 cc/kg as long as it is not allowed back into the thorax. It would typically be expelled after about 2 to 6 compression/recoil cycles. The volume of air expelled from the chest could be expelled against a low level of fixed or variable resistance, typically in the range from about 0 cm $H_2O$ to about 10 cm $H_2O$. This could be adjustable and could be provided by a valve system or other means having a flow of positive pressure gases, such as oxygen. This process can be further augmented by active compressions and active decompressions. This process can also be further augmented by actively extracting a volume of respiratory gases between positive pressure breaths, creating even more space in the thorax to be filled with blood with each decompression phase of CPR to prime the heart for the next compression.

Periodically the lungs need to be inflated so that the pulmonary vascular resistance (blood pressure in the blood vessels in the lungs) does not get too high (which happens when the lungs are empty and collapse) which would limit blood flow through the lungs. Periodic inflation of the lungs also provides oxygen and helps to clear carbon dioxide. This process is depicted graphically in FIG. 1. The left-Y axis shows the volume of respiratory gas in the lungs in liters and the X axis shows time in seconds. At point A, a positive pressure breath is delivered. Down and up arrows show when chest compression and decompression (in this example passive chest wall recoil) occurs. Changes in the volumes of respiratory gases in the lungs when using the invention are shown by the solid line. With each chest compression air is pushed out of the lungs, and not allowed back into the lungs because of the valve system. This results in a progressive decrease in respiratory gases within the lungs. The shaded area, labeled B, is the volume of respiratory gas that is expelled from the lungs with each chest compression. The total volume, shown by B, creates space that is filled by more blood returning to the heart and lungs during the decompression phase whenever a positive pressure is not being applied to the thorax by chest compressions. By contrast, changes in the volumes of respiratory gases in the lungs without the invention are shown by the hashed line. Each compression and chest wall recoil cycle is associated with a slight increase and decrease in pressures in the airway as respiratory gases move freely into and out of the lungs with each decompression and compression cycle.

A variety of valves may be coupled to the patient's airway to permit respiratory gases to escape from the lungs during chest compressions, while permitting periodic ventilation. One type of valve could be a one-way valve, typically used in combination with another one-way valve that opens in the opposite direction and which is biased in the closed position so that gases cannot enter the lungs during chest recoil or chest decompression. Other valves system that may be used is described in U.S. Pat. Nos. 5,692,498; 6,062,219; 6,526,973; and 6,604,523, incorporated herein by reference. With such valves, the threshold cracking pressure could be set high enough so that respiratory gases were always prevented from entering into the lungs until actively ventilated. In some embodiments, the pressure-responsive valve may be configured to remain closed during successive chest compressions in order to permit removal of at least about 2 ml/kg or 3 ml/kg from the lungs in order to lower intracranial pressure and increase cerebral brain flow to improve survival with favorable neurological function. For example, the pressure-responsive valve may be configured to remain closed during successive chest compressions in order to permit removal at least about 100 ml, preferably 200 ml, from the lungs of a 70 kg patient in order to lower intracranial pressure to improve survival with favorable neurological function. When respiratory gases are needed (such as when ventilating the patient after several successive chest compressions or if the patient begins to spontaneously breath), the pressure-responsive valve may be further configured to open after the negative pressure within the patient's airway reaches about −7 to −18 cm $H_2O$, at which time the pressure-responsive valve may be configured to open to provide respiratory gases to flow to the lungs through the pressure-responsive valve. In some cases, the pressure-responsive valve is configured so that when the pressure-responsive valve opens, it provides resistance to the incoming gas flow at a level of about 7 to about 18 cm $H_2O$ at a flow rate of 20 L/min.

Figure 2A:
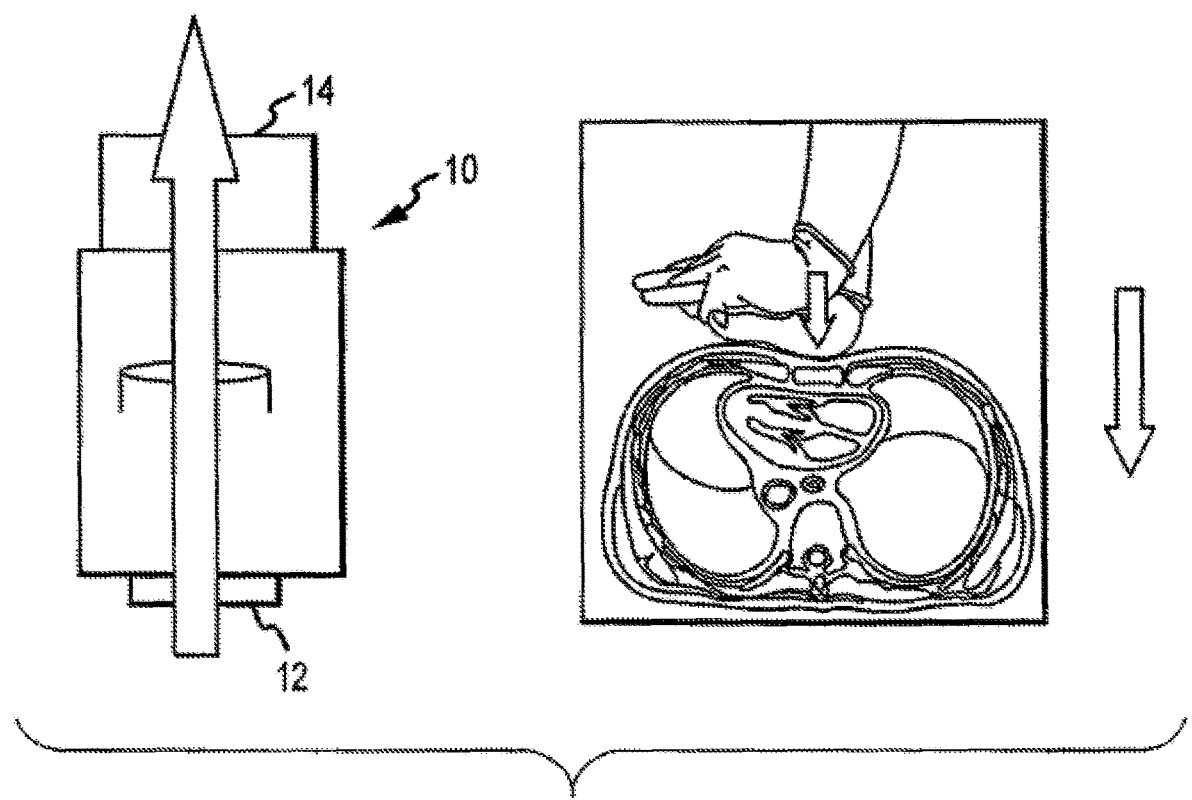
FIG. 2A schematically illustrates expired respiratory gases passing through a valve system during a chest compression according to the invention, along with a control system and a sensor.
Figure 2B:
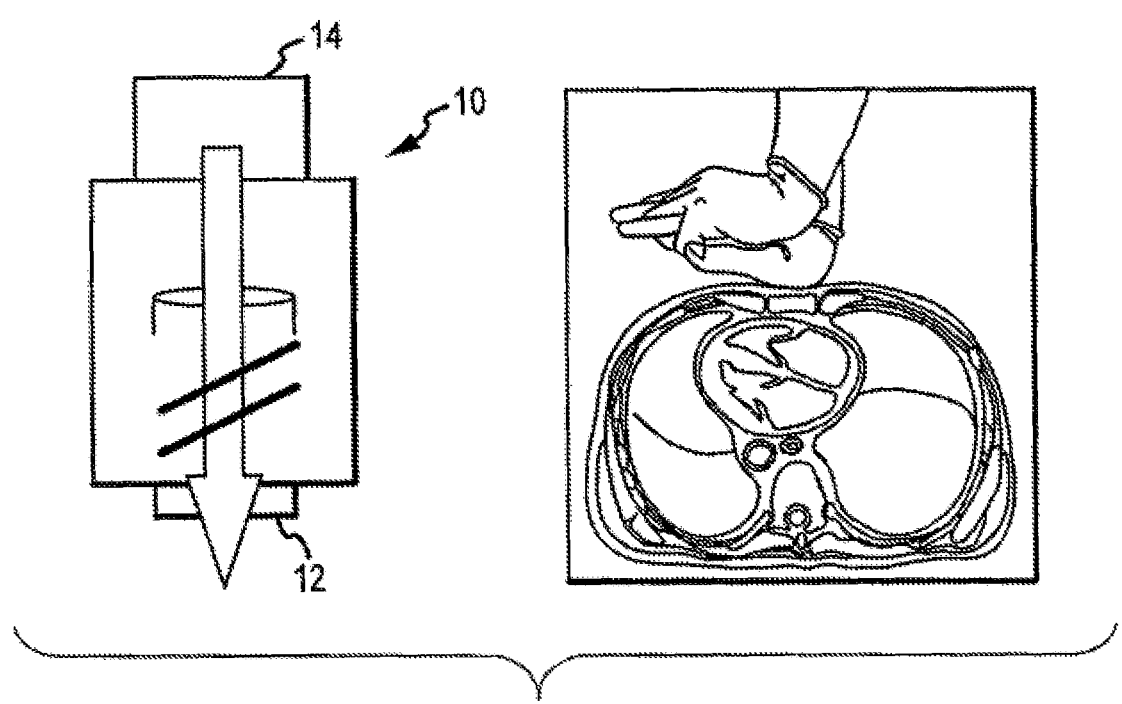
FIG. 2B schematically illustrates how respiratory gases are prevented from passing through the valve system and into the lungs during chest recoil or chest decompression according to the invention.
Figure 2C:
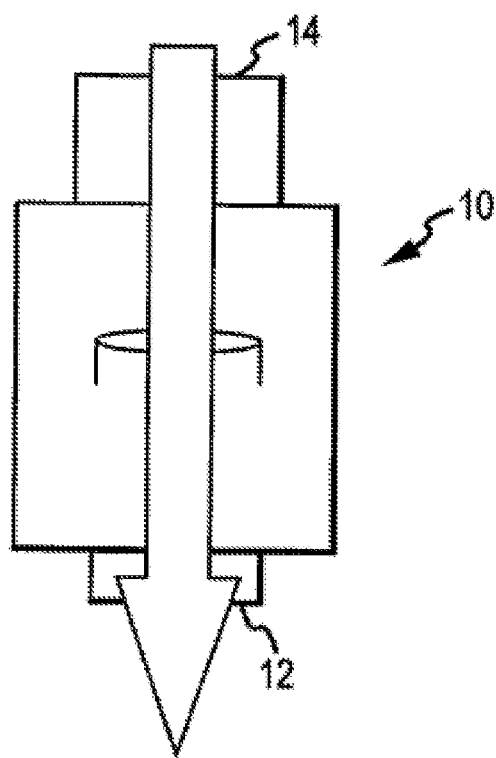
FIG. 2C schematically illustrates the injection of an oxygen-containing gas through the valve system to provide patient ventilation according to the invention.

Airflow into and out of the chest through one embodiment of the invention is shown schematically in FIGS. 2A-C. In FIG. 2A, a valve system 10 is schematically illustrated. Valve system 10 has a patient port 12 which interfaces with the patient's airway and a rescuer port 14 used by a rescuer to provide ventilation to the patient. When the chest is compressed (as illustrated by the hands pressing down on the chest wall), respiratory gases flow from the patient through the valve system 10 as shown by the arrow. In so doing, the respiratory gases pass into room air with minimal or no resistance from valve system 10. In FIG. 2B, the chest wall recoils during the decompression phase as the rescuer's hands are lifted (or the chest is actively lifted upward). Now, valve system 10 prevents respiratory gases from entering the patient. In FIG. 2C a positive pressure ventilation is delivered through rescuer port 14 wherein passes through valve system 10 and out patient port 12 where is passes to the patient's lungs. As such, with each chest compression, more and more gases are forced out of the lungs. This is because during decompression, gases are prevented from entering. When needed, gases can be injected into the lungs to provide adequate ventilation.

Figure 2D:
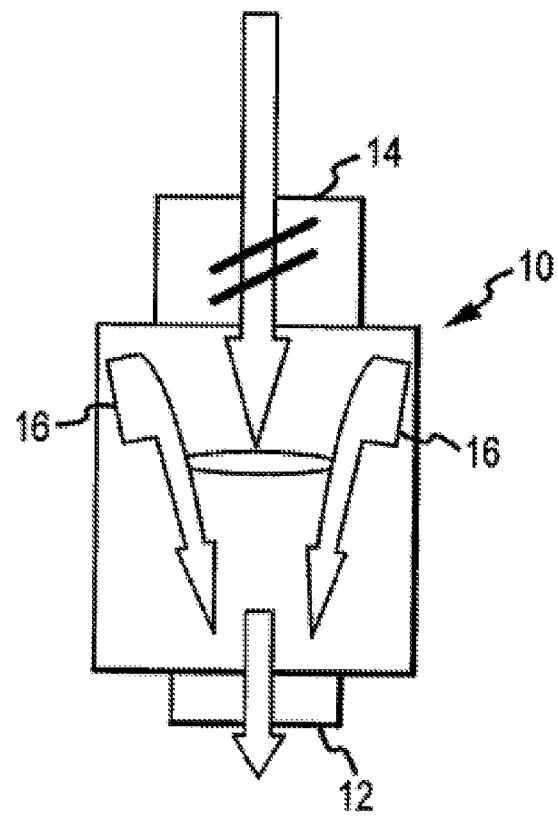
FIG. 2D schematically illustrates the passage of respiratory gases through a safety check valve if the patient inspires according to the invention.

In some cases, the patient may begin to breathe or gasp spontaneously. As shown in FIG. 2D, valve system 10 has one or more safety check valves 16 to permit gases to pass through patient port 12 and into the lungs. As one example, safety check valves 16 may be set to open at about −10 cm $H_2O$. This schematic is not meant to be limiting but rather demonstrative of airflow through one potential embodiment of the invention during CPR.

The invention may employ a variety of techniques to enhance circulation. For example, a device to augment circulation during the performance of cardiopulmonary resuscitation in a patient in cardiac arrest may be configured to allow a volume of respiratory gas from the lungs to exit the airway with each external chest compression but prevents oxygen containing gases from passively reentering the lungs each time the chest wall recoils. This may be done using a valve system having a one-way valve and a means to periodically expand the lungs with oxygen-containing gases. Such a device may be particularly useful when the chest is compressed and allowed to recoil at a rate of about 60 to about 120 times/min and even more useful with a range of 90 to 110 times/min. Such a device may also permit a volume of respiratory gases to be expelled from the lungs with each compression. Such a device can be used with manual CPR, ACD CPR, manually operated CPR devices, or automated CPR devices. With each chest wall recoil, respiratory gases are prevented from returning to the lungs by means of a one-way valve. Over each successive chest compression/chest recoil cycle there is a successive decrease in respiratory gases within the lungs. Periodically, the lungs are actively expanded with oxygen-containing gas.

The valve system can be made of one or more check valves, spring valves, duck valves, other mechanical or electronically controlled valves and switches. The lungs are periodically expanded by a ventilation source that could include: mouth-mouth ventilation, mouth-mask, a resuscitator bag, an automatic or semi-automatic ventilator, a body cuirass or iron-lung like device, or the like. A variety of sensors could be incorporated into the system to guide the ventilation rate and/or determine the degree of chest compression and/or degree of chest wall recoil including: airway pressure sensors, carbon dioxide sensors, motion detectors, force detectors, and/or impedance sensors to detect air/blood ratio in the thorax to help guide ventilation and compression rate.

The valve system could include a one-way valve with a means to impede exhalation or the exodus of respiratory gases with a fixed or variable resistance. This could be in the range from about 0 to about 20 cm $H_2O$, and in some cases about 0 to about 10 cm $H_2O$. This may also be adjustable. In some cases such expiratory resistance helps to push blood out of the lungs back into the left heart, and serves as a means to help prevent buildup of blood in the lungs during CPR.

Figure 3A:
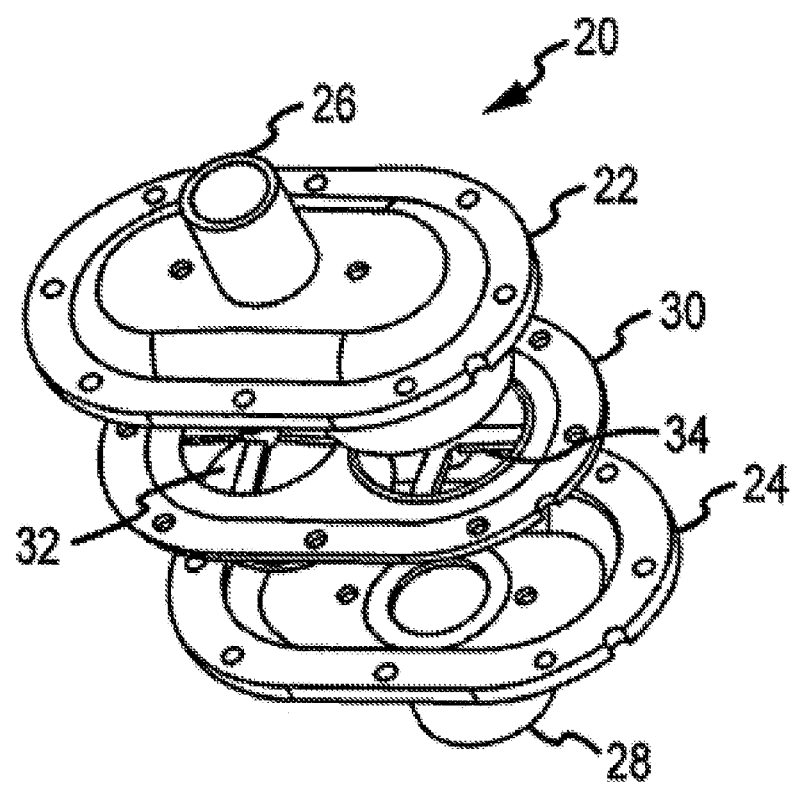
FIG. 3A illustrates one embodiment of a valve system according to the invention.

One particular embodiment of a valve system 20 is shown in FIG. 3A. Valve system 20 is constructed of a housing, which is conveniently manufactured as an inspiration interface housing 22 and a patient interface housing 24. A ventilation source port 26 for ventilation to the patient is included in housing 22 while a connector port 28 is included in housing 24. In this way, a ventilation source may be coupled to port 26 and port 28 may be used to interface with the patient, and the patient's airway. A valve plate 30 having a pair of one-way check valves 32 and 34 in between.

Figure 3B:
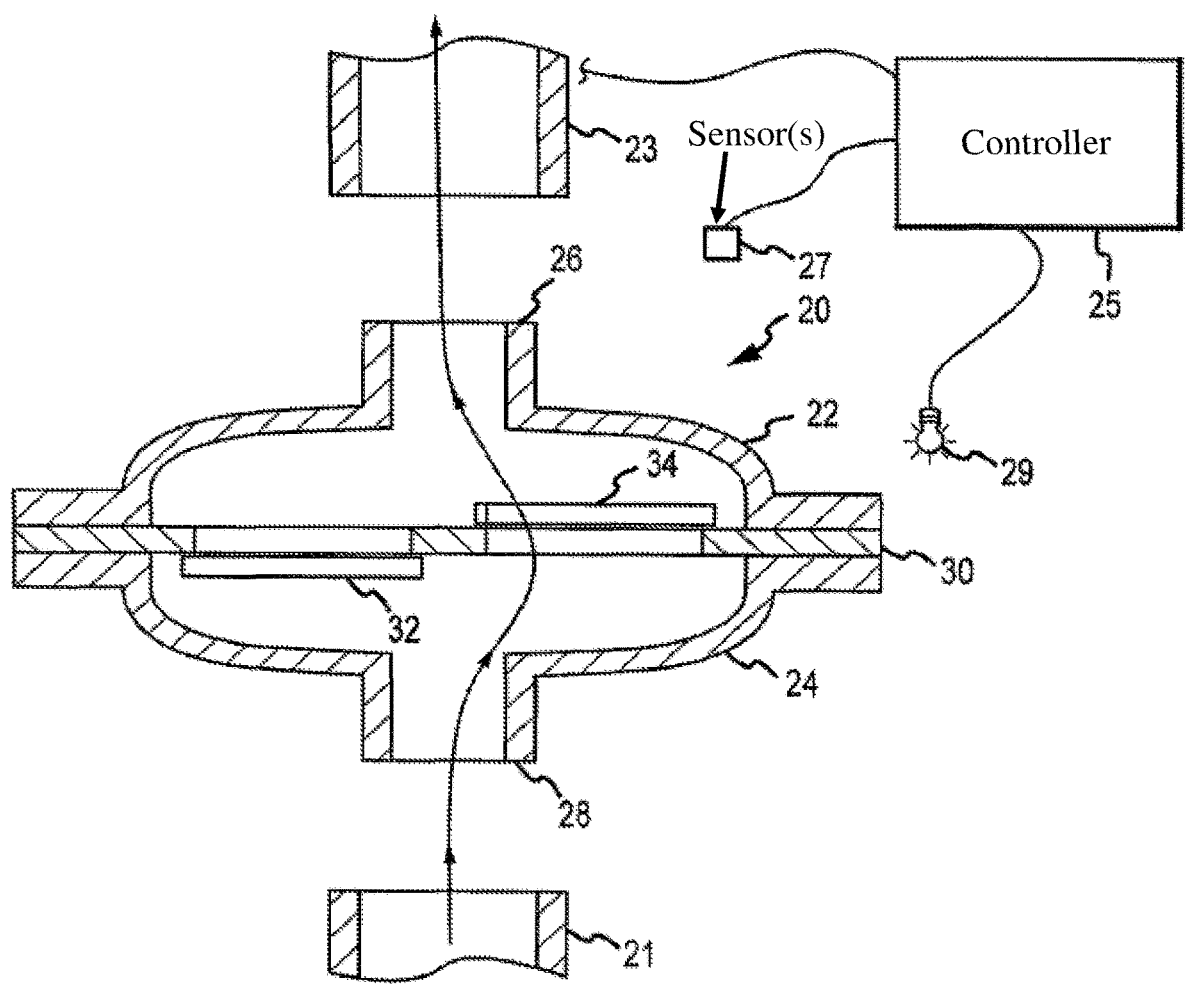
FIG. 3B is a cross sectional side view of the valve system of FIG. 3A illustrating gas flows with patient exhalation (such as during a chest compression), along with a control system and a sensor.

As shown in FIG. 3B, during chest compression, respiratory gases flow from the patient and pass through port 28 where the gases open expiratory check valve 34. From there, the gases exhaust to the atmosphere through port 26. Optionally, valve 34 may be biased in the closed position, and may open when the exiting gases exert a pressure that is less than about 20 cm $H_2O$.

Port 28 may be coupled to a patient interface 21, which could include a facial mask, endotracheal tube, other airway device or any of the other interfaces described herein. Port 26 may be coupled to a ventilation source 23, such as a ventilator bag, ventilator, tube for performing mouth-to-mouth resuscitation, or any of the other devices described herein.

Further, a controller 25 may be employed to control any of the electronic equipment. Controller 25 may include a storage device, such as memory, one or more processors and appropriate hardware, and/or software for performing operations under the direction of the processor. For example, if ventilation source 23 were a ventilator, controller 25 may be employed to control operation of the ventilator. One or more sensors 27 may be coupled to controller to monitor various physiological parameters of the patient as described herein. Also, controller 25 could modify application of chest compressions and/or ventilations based on the sensed parameters.

Controller 25 may also be coupled to one or more timing lights 29 which could be used to indicate to a rescuer as to when to provide chest compressions and/or ventilations.

Figure 3C:
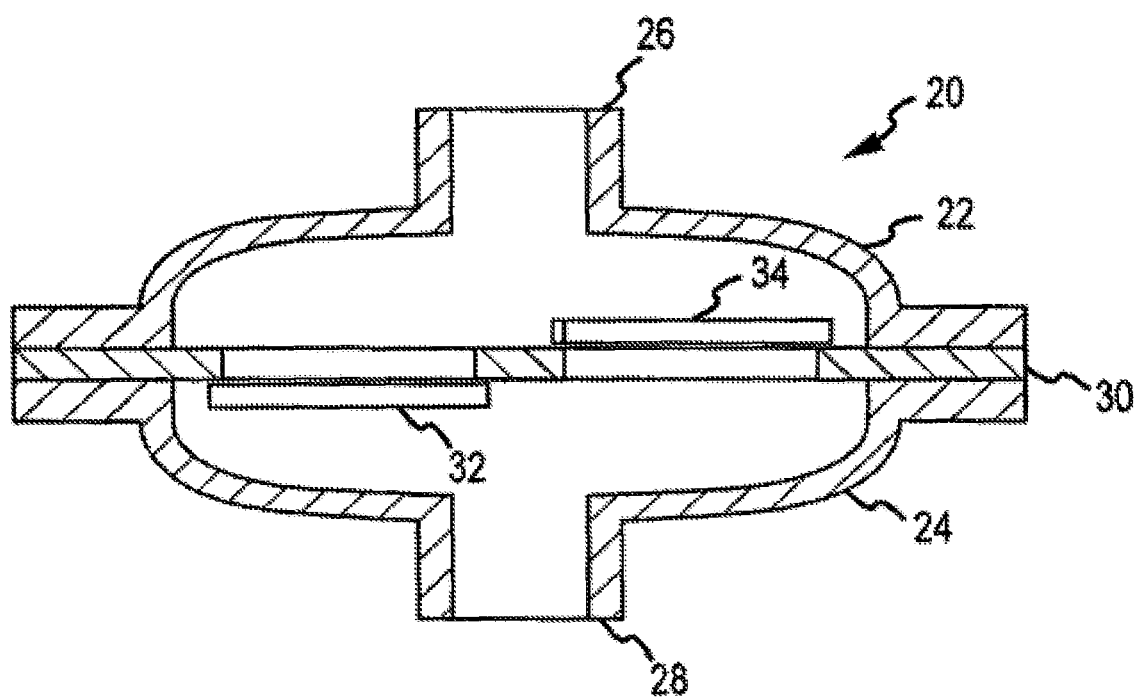
FIG. 3C is a cross sectional side view of the valve system of FIG. 3A illustrating the absence of gas flow when the patient's chest recoils or is lifted.
Figure 3D:
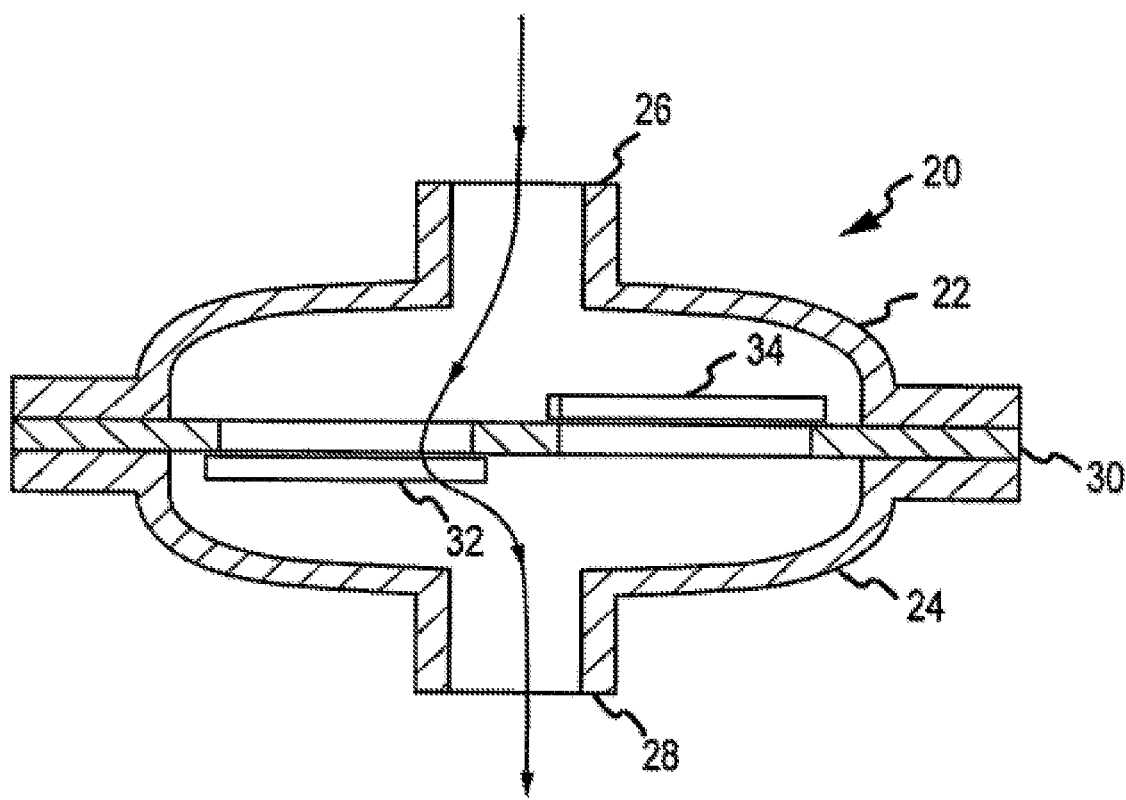
FIG. 3D is a cross sectional side view of the valve system of FIG. 3A illustrating gas flows when delivering an oxygen-containing gas to the patient.

In FIG. 3C, the chest wall recoils. Inspiratory check valve 32 is biased in the closed position, by use of a spring, elastomer or the like, so that no respiratory gases are allowed through inspiratory check valve 32. Valve 32 may be biased closed until a pressure in the range of about −5 to about −10 mmHg is achieved. This is most likely to occur when the patient takes a spontaneous gasp during CPR, and then airflow moves through the inspiratory check valve 32 to the patient through port 28. This can also occur if a rescuer ventilates the patient rapidly with a large tidal volume rapidly through port 26 as shown in FIG. 3D.

Another exemplary valve system that functions in a similar manner is the ResQPOD® ITD valve system, commercially available from Advanced Circulatory Systems. Such a valve system is also described in U.S. Pat. No. 8,408,204 and U.S. patent application Ser. No. 14/197,996, both of which are incorporated herein by reference. Such a valve system was used to generate the data described hereinafter with reference to the Example.

Any of the valve systems described herein could also include or be associated with physiological sensors, timing lights, impedance sensors to detect air/blood ratio in the thorax, and a way to communicate with a CPR device or other apparatus used during resuscitation (e.g. defibrillator) to provide feedback in terms of how to perform CPR, the optimal time to actively inflate the lungs with respiratory gases or the optimal time to defibrillate. For example, the feedback could be used to determine the proper rate of chest compressions, the proper depth of chest compressions and/or the proper rate or volume of ventilations.

The valve systems or associated devices could also include a way to deliver a low flow and volume of continuous oxygen into the lungs which is less than or just equal to the total volume of the expelled volume of respiratory gases with chest compressions so that the number of times that the lungs are expanded with oxygen-rich gases is reduced by the low level of continuous oxygen insufflation.

Figure 4:
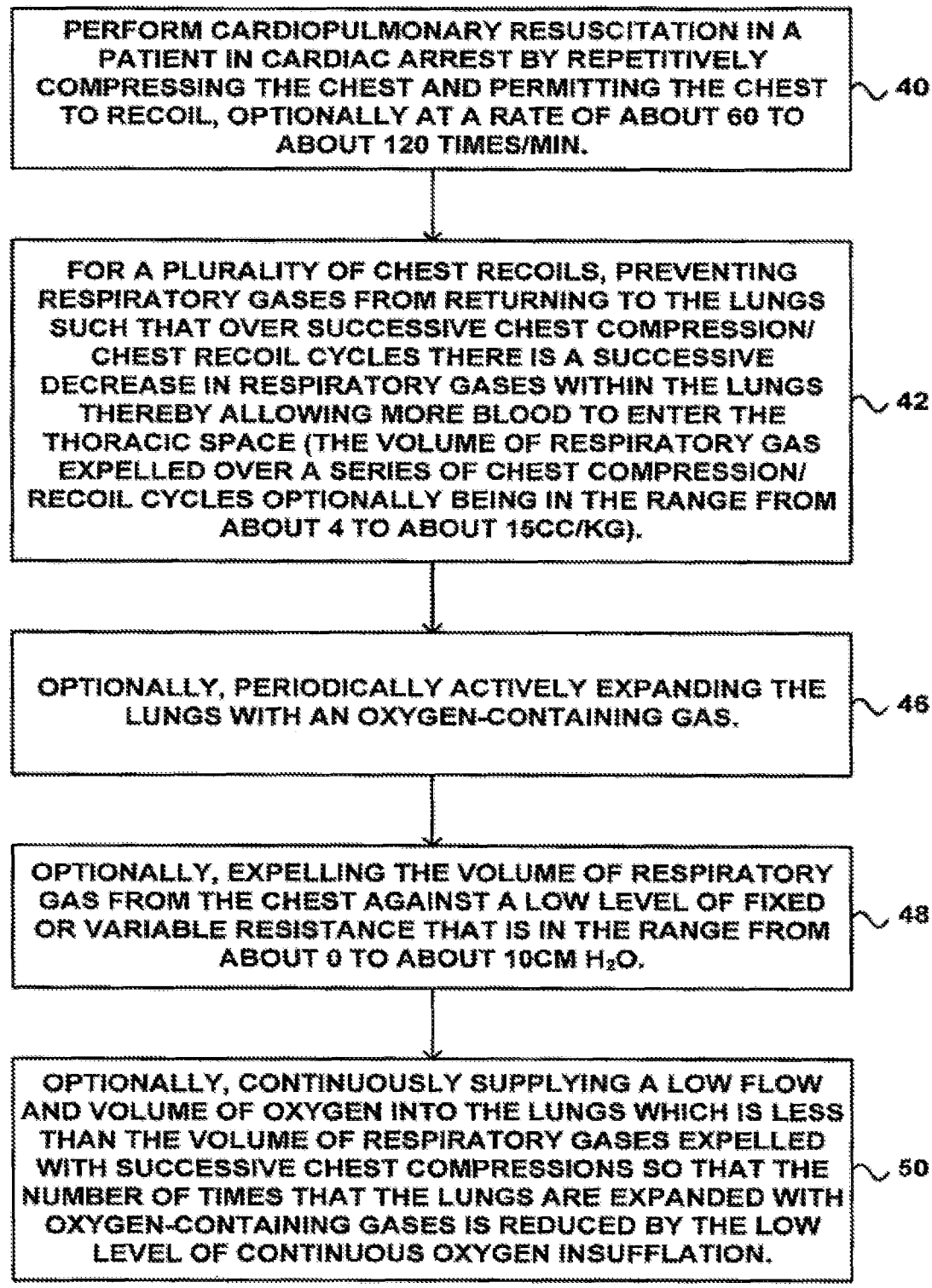
FIG. 4 is a flow chart illustrating one method for performing CPR according to the invention.

One method for controlling gas flow into and out of a patient's lungs is illustrated in FIG. 4. At step 40, cardiopulmonary resuscitation is performed on a patient in cardiac arrest. This may be performed by compressing the chest and allowing the chest to recoil at a rate of about 60 to about 120 times per minute, but preferably between 90 and 110 times per minute.

For a plurality of chest recoils, respiratory gases are prevented from returning to the lungs such that over successive chest compression/chest recoil cycles there is a successive decrease in respiratory gases within the lungs (see step 42). This allows more blood to enter the thoracic space (the volume of respiratory gas expelled over a series of chest compression/recoil cycles optionally being in the range from about 4 to about 15 cc/kg). Hence, over each successive chest compression/chest recoil cycle there is a successive decrease in respiratory gases within the lungs thereby allowing more blood to enter the thoracic space.

Periodically, the patient may be ventilated (see step 46), such as by periodically actively expanding the lungs with an oxygen-containing gas. During the chest recoil phase of CPR, intracranial pressures are decreased more rapidly and to a lower value thereby further increasing the duration and magnitude of cerebral perfusion pressure. Optionally, the volume of respiratory gas expelled from the chest may be expelled against a low level of fixed or variable resistance that is in the range from about 0 to about 10 cm $H_2O$ (see step 48).

The devices and methods described herein may be used with any type of CPR technique that involves manipulation of the chest to change pressures within the thorax would benefit from this improved method of invention. Also, the method for providing periodic expansion of the lungs could include mouth-mouth ventilation, a resuscitator bag, an automatic or semi-automatic ventilator, an anesthesia machine, a body cuirass or iron-lung like device. The method could also include a way to deliver a low flow and volume of continuous oxygen into the lungs which is less than the total volume of the expelled volume of respiratory gases so that the frequency of positive pressure ventilations by an external ventilation source could be reduced by the low level of continuous oxygen insufflation (see step 50).

A variety of sensors could be used to guide the periodic ventilation rate or determine the rate and/or depth of chest compression or degree of chest wall recoil. Sensors could include airway pressure sensors, timing lights, carbon dioxide sensor, electrocardiogram signal sensors, motion detectors, force detectors, and/or impedance sensors to detect air/blood ratio in the thorax to help guide ventilation and compression rate and determine if CPR should be continued, the optimal time and way to defibrillate, and when to stop CPR efforts because of futility.

The method could include a number of different airway adjuncts to maintain a seal between the trachea and the ventilation source or pharynx and ventilation source or mouth and ventilation source (e.g. endotracheal tube, face mask, laryngeal mask airway, supraglottic airway, and the like). Sensors within these airways could be used to verify proper airway adjunct placement. Such sensors could include a carbon dioxide detector which could be housed in a manner that is protected from bodily fluids.

The method could include a means to transmit the amount of respiratory gas volume delivered or expelled from the chest to a monitoring system that could be used as part of a closed loop circuit to maximize the number of compressions interspersed between active ventilations in order to maximize circulation during CPR. Circulation during CPR could be measured by a variety of means including measurement of end tidal carbon dioxide, the change in expired end tidal carbon dioxide levels over a given time interval, measurement of other respiratory gases, a change in impedance within the body, and changes in other physiological parameters such as temperature.

In some embodiments, the invention provides the ability to utilize one or more sensors that are associated with the valve systems described herein to indirectly measure the rate and depth of chest compression. For instance, the sensors may measure the respiratory gases (also referred to as "air") delivered to the patient, the airway pressure and the like, and then used to estimate the rate and depth of chest compression. This provides a convenient way to measure the quality of CPR. This may be done, for example, by comparing variations in amount of air delivered (or airway pressure) produced by positive-pressure ventilation to the air expelled (or airway pressure variations) produced during chest compressions. This provides an easy way to monitor, analyze and report the depth of compressions, particularly to the user in real time. This feedback allows the user an opportunity to continuously adjust or change the depth of manual (or automatic) compressions to achieve a targeted depth of compressions. Also, the pressure or volume of air generated by positive-pressure ventilation or delivered by a manual resuscitation bag can be analyzed and reported to the caregiver for monitoring and adjustment purposes. In addition to calculations which report actual compression depth and breathing pressure, the frequency and duration of both breaths and compressions can be monitored and reported to the user. Hence, frequency of compressions and ventilation can be controlled to provide a targeted frequency or rate.

As one example, measurements may be taken using one or more sensors disposed anywhere within valve system 20, such as within the housing or one of the valves. For example, a sensor could be disposed in inspiration interface housing 22 or in patient interface housing 24. As another option, the sensor could be positioned within ventilation source port 26, or within one-way check valves 32 or 34. Pressure or air volume measurements may be transmitted to a controller, such as controller 25, either wirelessly or by a wired connection. Controller 25 may be programmed to determine the depth of chest compressions, timing, frequency, and the like, as described above using the pressure or air volume readings. Further, various visual and/or audio signals may be provided to the rescuer giving feedback as to depth or compressions, rate of compressions, rate of ventilation and the like. Controller 25 may be programmed to provide this feedback, such as to timing lights, computer display screens, speakers, and the like.

ITD and CPR

Volume exchange, the movement of air out of the thorax and blood into the thorax, during CPR can be a factor not only in the survival of a patient, but also in increasing neurological function in a patient after cardiac arrest. Increases in survival with increased neurological function may be realized when chest compressions are performed at a proper rate and depth in conjunction with the use of an ITD that may be configured to be coupled to a patient's airway. The ITD may be similar to any of the ITDs described herein, including the ResQPOD® ITD as described in U.S. Pat. No. 8,408,204 and U.S. patent application Ser. No. 14/197,996, both of which are incorporated herein by reference. With standard CPR (when chest compressions are being performed at a rate between 90 to 110 compressions per minute and at a depth of 4.5 cm per compression to about 6 cm per compression) in conjunction with such an ITD, the intracranial pressure is lowered to improve survival with favorable neurological function. These rates may apply for either manual or automated standard CPR. However, it will be appreciated that the optimal ranges may vary depending on the method of CPR used. For example, ACD-CPR may have a different range of compression rate and/or depth. Additionally, the choice of ITD or intrathoracic pressure regulation (ITPR) device may alter the optimum range of compression rate and/or depth. Along with increased intracranial pressure and survival rates, usage of an ITD with proper CPR may increase blood flow to the heart and brain. In some cases blood flow to the heart may be doubled and blood flow to the brain increased by up to 50%. The combination of ITD and proper CPR as described above may also result in up to a twofold increase of systolic blood pressure, while increasing the likelihood of successful defibrillation.

In some embodiments, an ITD may be used in conjunction with proper standard CPR. The compression rate and/or depth may be monitored and/or directed using a guidance device. For example, a guidance device may include a light emitting diode or other light producing device and/or a speaker that may produce audible sounds. The lights and/or sounds may be produced at a rate of proper chest compressions, such as between 80-120 compressions/minute, more preferably between 90-110 compressions/minute. The guidance device may also include a load cell, accelerometer, and/or other device to accurately monitor the chest compressions. Such sensors allow the guidance device to produce a visual and/or audible signal as feedback to a user that the chest compression rate and/or depth is above, below, or within a proper range. In some embodiments, the guidance device may include CPR assist devices as described herein.

Embodiments of the present invention may use a variety of devices to perform chest compressions in a repeated manner (in combination with the use of the ITD as just described). As one example, the chest compression device may enable manual and automated cardiopulmonary resuscitation (CPR), optionally in combination with electrocardiographic monitoring (ECM) and/or electrical defibrillation as part of advanced cardiac life support (ACLS) procedures. One chest compression device that may be used is described in U.S. Pat. No. 8,702,633, the entire contents of which is herein incorporated by reference.

Such a compression device is well suited for administering enhanced active compression/decompression (ACD) CPR and ACLS procedures, as well as standard CPR procedures. In some cases, the compression device may include a disposable adhesive pad which sticks to the chest of the patient, a detachable handle that detaches from the adhesive pad when excessive decompression force (upward pull) is applied, and a display which indicates to the operator the appropriate amount of force to be applied. Moreover, the device can be configured or customized for use on a particular individual based on body weight or size.

ACD CPR systems and techniques provided herein can enable a rescuer or operator to perform ACD CPR, which differs from standard CPR in that it actively re-expands (decompresses) the chest after each compression. This approach allows the operator to use the same body position and compression technique as in standard CPR. Active chest decompression is achieved when the rescuer maintains a firm grip on the ACD CPR system and swings his or her body weight upwards after compression. A single-use disposable adhesive pad can be applied to the chest and transfers the lifting force to the lower part of the ribcage. Compression force is transferred to the chest as in standard CPR via the device's piston and compression pad. A force gauge in the handle assists the rescuer in applying the force needed to achieve desired compression (e.g. 4.5 to 6 cm), and the lift necessary for adequate decompression. A visual metronome can guide the rescuer to compress and decompress at the appropriate rate and force. For example, the visual metronome or other indicator mechanism may guide a user to deliver chest compressions at a rate of between about 90 and 110 compressions per minute. The force gauge and/or visual metronome may provide feedback to a user, such as by illuminating one or more lights when a user within or out of the optimum ranges of compression depth and/or compression rate.

In some embodiments, one or more colors of lights or displays on a screen of the chest compression device may be used to differentiate when a user is within an optimum range and when a user is outside of the optimum range. For example, a green light may illuminate when a user is compressing a patient's chest within an optimum range, while a red light may indicate that a user is compressing the patient's chest either too little or too much. In other embodiments, different colors may be used for too much or too little compression to further guide a user. Lights may also be used to direct a user to compress the patient's chest at a particular rate. For example, one color of light may be used to indicate that a compression rate is within a desired range, while a second color of light may indicate that a user is compressing the chest too slowly or too quickly. Alternatively, a light may flash at the optimum compression rate to help guide a user. In some embodiments, audio signals, such as sounds produced from a speaker of the chest compression device, may be produced to help alert a user if a compression depth and/or rate is within or out of an optimum range.

In use, the operator can attach the system with the patient's chest via the adhesive pad, and apply compressive and decompressive forces to the patient by maneuvering the system handle. For example, the operator can press downwardly on the handle with a sufficient force so as to compress the patient's chest and induce blood circulation from the chest. The operator can then pulls upwardly on the handle so that the adhesive pad actively expands the patient's chest to induce blood circulation into the chest and ventilate the patient's lungs. The downward and upward strokes can be repeated at a rate sufficient to maintain blood circulation and enhance ventilation, typically with a compression distance in the range from about 4.5 cm to about 6 cm and a rate in the range from about 80 repetitions to about 110 repetitions per minute. This technique may be particularly effective when the operator kneels beside the patient and grasps the handle with fully-extended arms, with the operator's palms engaging the upper surface of the handle and fingers grasped around the peripheral flange of the handle. The operator may then apply the necessary or desired downward and upward strokes with fully-extended, locked arms while holding the system in a very stable configuration.

Figure 5:
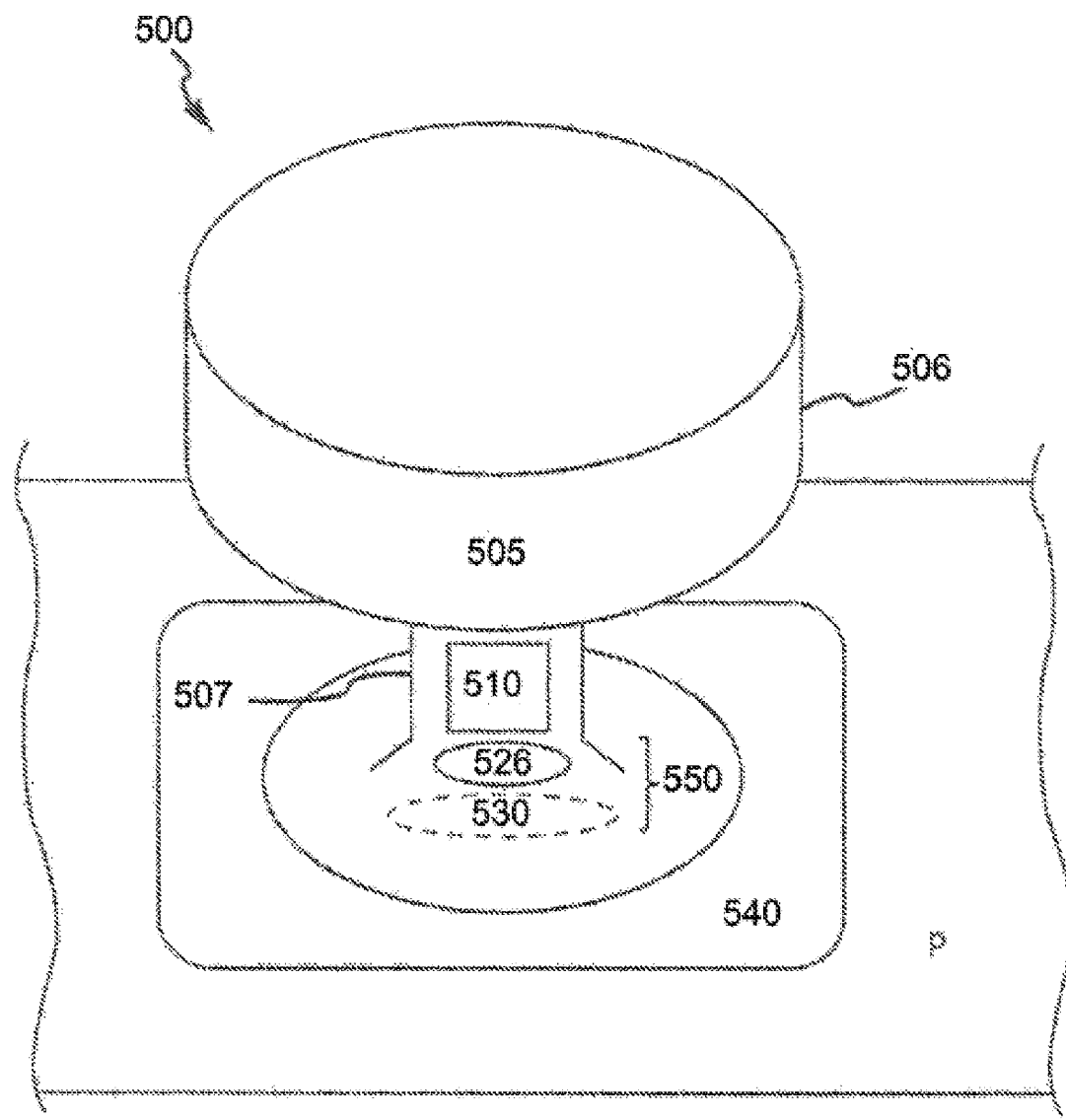
FIG. 5 illustrates an embodiment of an ACD CPR system according to embodiments.

FIG. 5 illustrates aspects of one ACD CPR system according to embodiments of the present invention. A stem 507 of a system handle 505 contains a load cell 510 that measures the compression and decompression forces applied to the patient P. In some embodiments, the load cell 510 which measures the compression and decompression forces is in compression during its resting state. Accordingly, the load cell 510 can provide measurements for both upward and downward forces. The handle 505 can be designed to provide a convenient grip 506 that transfers compression via the heels of the hand and lift via the fingers. Hence, no change of grip may be needed between compression and decompression. System 500 may be configured so that the handle 505 is automatically positioned by magnets 520, 530 when the handle 505 comes into contact with an adhesive pad 540. According so some embodiments, system 500 may include a detachable magnetic connection mechanism 550 disposed between the handle 505 and the adhesive pad 540. The connection mechanism 550 can be configured so that the handle 505 decouples from the adhesive pad 540 on the chest when the decompression force exceeds a predetermined limit. For example, the handle 505 may become unattached at a pull force of 25 lbs, thereby not allowing the user to pull up with more than 25 lbs force. Furthermore, the handle 505 can be easily attached to the adhesive pad 540 when it is brought close to the pad 540 via the magnetic interlock or connection mechanism 550.

Figure 5A:
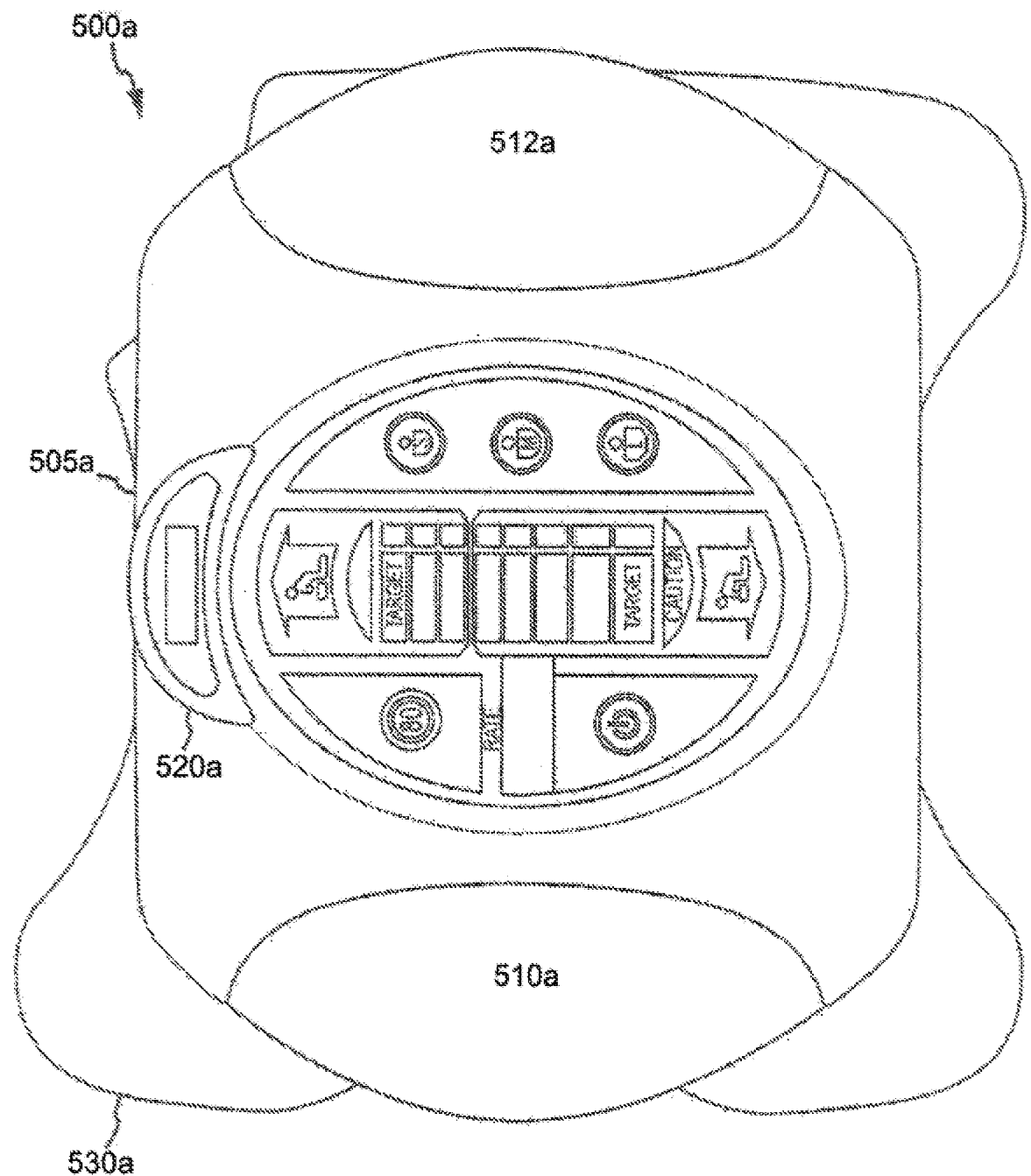
FIG. 5A provides a top view of the ACD CPR system of FIG. 5 according to embodiments.

FIG. 5A provides a top view of an ACD CPR system 500a according to embodiments of the invention. System 500a includes a handle 505a having two handgrips 510a, 512a and a graphical user interface 520a. Handle 505a is intended for multiple uses and is easily attached and removed from an adhesive pad 530a. In some cases, adhesive pad 530a is disposable. For example, in use the adhesive pad may be applied to a patient during an ACD CPR procedure, and discarded following the treatment. Handle 505a may be attached with adhesive pad 530a via a magnet. In some instances, the magnetic coupling is configured such that handle 505a becomes detached from adhesive pad 530a when excessive decompression force (upward pull) is applied. Other means to couple the handle to the adhesive pad include various mechanical connections including ball and socket, cantilevered arm, or detent mechanism or the like.

Figure 5B:
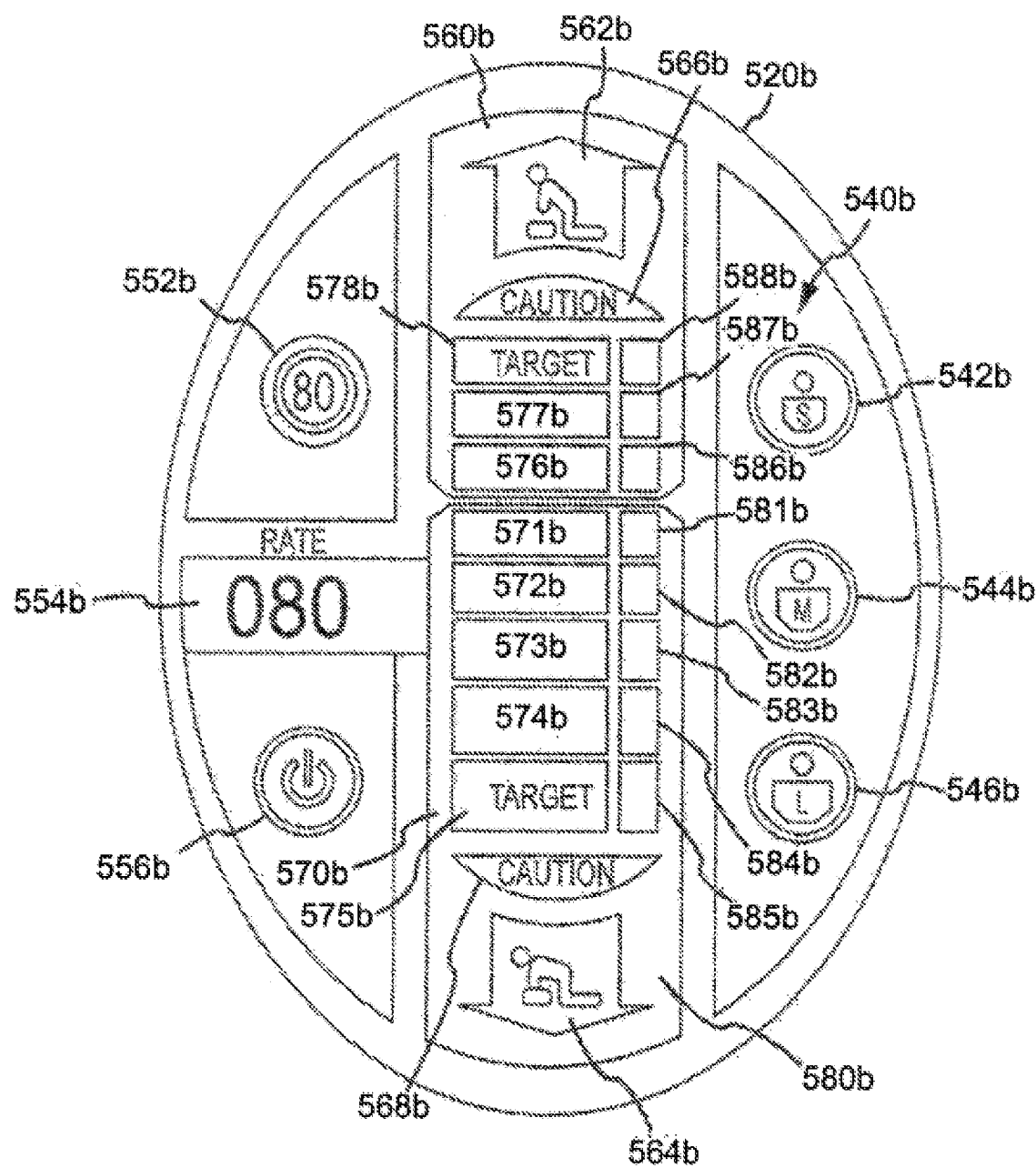
FIG. 5B depicts a graphical user interface (GUI) according to embodiments.

FIG. 5B depicts an exemplary graphical user interface (GUI) 520b according to embodiments of the present invention. As shown here, GUI 520b includes a body size input 540b having a small body size selection 542b, a medium body size selection 544b, and a large body size selection 546b. These three inputs or buttons allow a user to select the patient chest size or stiffness. GUI 520b also includes a target compression/decompression numerical rate display 552b, an actual or applied compression/decompression numerical rate display 554b, and a power indicator or button 556b. Target rate display 552b can be configured to provide a numerical display or output of the desired or appropriate compression rate, decompression rate, or both. Actual rate display 554b can be configured to provide a numerical display of the actual or applied compression rate, decompression rate, or both. Further, GUI 520b includes a force application display 560b that includes a force guide 570b and a force display 580b.

Force guide 570b provides an indication or guide to the operator of how hard to push during a chest compression, how hard to pull during a chest decompression, and how fast to push and pull while administering the compressions and decompressions. For example, in some cases the system may determine that a compression force of 100 lbs and a decompression force of 20 lbs should be applied during the treatment, at a rate of 100 compressions per minute. During the compression and decompression phases of the cycle, indicator bars 571b-578b light up or activate in sequence at the prescribed rate, to provide the operator with a visual guide of how forcefully and how quickly to administer the compressions and decompressions.

Force display 580b provides an indication of how hard the operator is actually pushing during the compression phase and pulling during the decompression phase, and how fast the operator is pushing and pulling when administering the compressions and decompressions. For example, during the compression and decompression phases of the cycle, indicator bars 581b-588b light up or activate depending on how forcefully and how quickly the operator administers the compressions and decompressions. Accordingly, force display 580b enables the operator to track or visualize his or her actual applied force and rate, and compare the applied force and rate with the target force and rate as provided by force guide 570b. By using force guide 570b as a target reference and force display 580b as an indication of the efforts applied during treatment, the operator can realize or approach the goal of matching the applied forces and rates with the target forces and rates.

Force application display 560b also includes a decompression indicator 562b, a compression indicator 564b, a decompression limit warning indicator 566b, and a compression limit warning indicator 568b. According to the embodiment depicted here, decompression indicator 562b provides the user with a reference or indication that force guide 570b and force display 580b signals displayed toward the top of GUI 520b are associated with the decompression phase of ACD CPR Likewise, compression indicator 564b provides the user with a reference or indication that force guide 570b and force display 580b signals displayed toward the bottom of GUI 520b are associated with the compression phase of ACD CPR. The system can be configured so that decompression limit warning indicator 566b lights up or activates when the operator applies a decompression force that exceeds a prescribed decompression force or force range. Similarly, system can be configured so that compression limit warning indicator 568b lights up or activates when the operator applies a compression force that exceeds a prescribed decompression force or force range. These features can help the operator avoid application of excessive forces during treatment, which in some cases could cause injury to the patient.

In some cases, red caution lights may illuminate when the applied force exceeds the prescribed force range. For example, if the operator approaches or exceeds the decompression target limit, a caution light may illuminate and the handle can disconnect from the adhesive pad either immediately or shortly thereafter. In the event the handle becomes detached, the rescuer may reattach the handle by bringing the handle close to the adhesive pad, whereby the handle and the adhesive pad are coupled via magnetic attraction. Once the handle and the pad are attached, the operator can resume the compression and decompression actions of the ACD CPR method. The rescuer can avoid or minimize frequent handle detachment by following the direction provided by a force guide.

When preparing the system for use on a patient, the operator can power on the system by pushing the power button 556b. According to some embodiments, the lights on the right side of the display will illuminate in response to activation of the power switch. In some cases, the operator may take caution not to push on the chest when pressing the power button. For example, in order for the force gauge to appropriately calibrate, it may be beneficial to have no load placed on the handle when the system is initially powered on.

In many instances, it is beneficial for the operator to compress the chest a certain number of times (e.g. about 30) without actively pulling up beyond neutral or applying a decompression force, to ensure appropriate adhesion of the adhesive pad before beginning active decompressions. Hence, the system can be configured or programmed to illuminate the guiding light or force guide 570b so as to guide the user to perform a certain number of compressions (e.g. about 30) before beginning ACD CPR. For example, the force guide 570b may initiate a series of signal displays for indicators 571b-575b (compression phase), but not for indicators 576b-578b (decompression phase). When the predetermined number of compressions are complete, the guiding light or force guide 570b can then direct the operator to compress and decompress in accordance with ACD CPR procedures.

Figure 6:
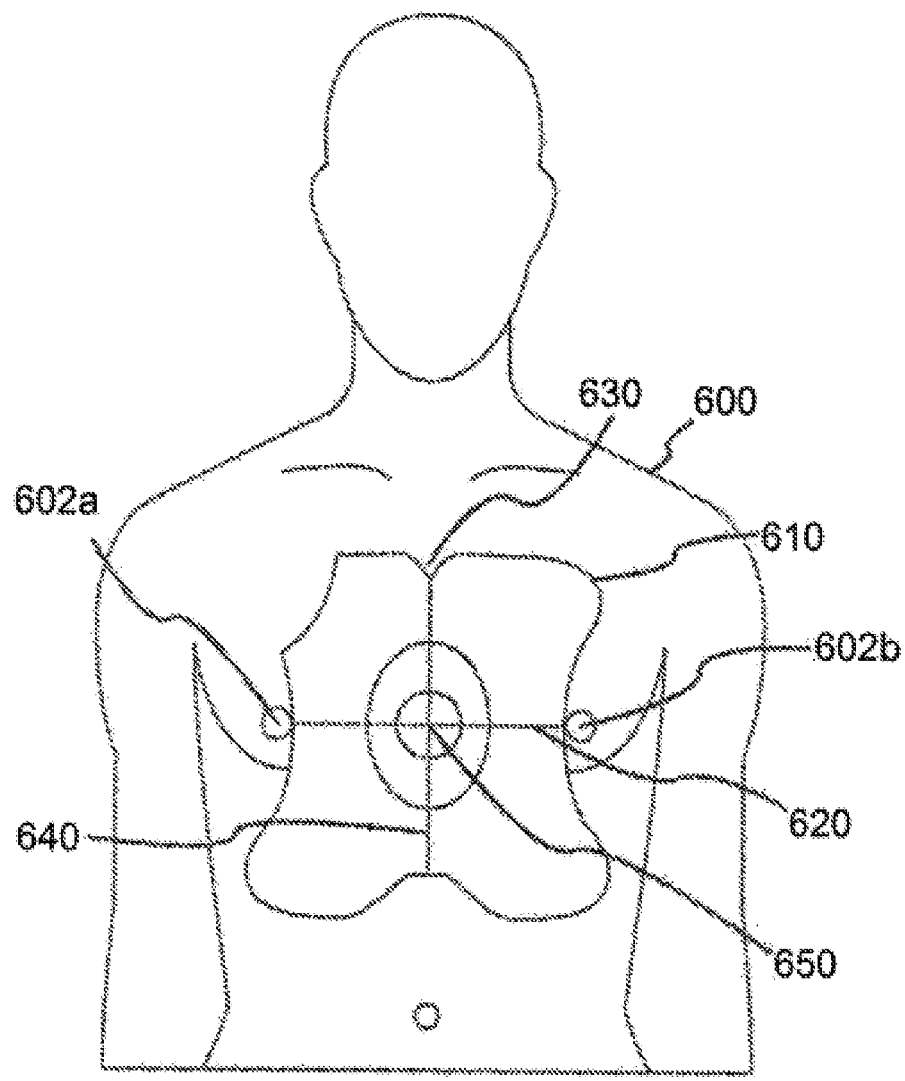
FIG. 6 shows an adhesive pad placement on a patient according to embodiments.

FIG. 6 shows an example of adhesive pad placement on a patient, according to embodiments of the present invention. As depicted here, an adhesive pad 610 is placed on patient 600, such that a nipple line 620 of pad 610 extends between the patient's nipples 602a, 602b. Further, adhesive pad 610 is placed such that sternum notch 630 of pad 610 is placed in the center of the patient's chest, directly over the sternum. Adhesive pad 610 may have a sternum line 640 which can be placed in alignment with the patient's sternum. When applying the system to the patient, the operator may orient the system such that the compression point of the system, which can be aligned with an adhesive pad compression point 650, is on the lower half of the sternum or center of the chest, which is at or near the compression point as prescribed in manual CPR techniques. Details of such an adhesive pad, as well as details of the electronics, other hardware and software included in the system may also be found in U.S. patent application Ser. No. 13/554,986, incorporated herein by reference.

It may be desirable to provide at least one element associated with the device that can measure a physiological parameter and/or display patient status information and/or feedback to the person performing the CPR. Preferably, the measuring element is associated with the surface element. Examples of physiological parameters include ventilation rates, temperature, blood pressure, heart rate, respiratory rate, and other vital signs. Some parameters may require separate monitoring devices (not illustrated) attached to the patient, and the display on the device makes the information immediately available to the person performing the CPR. Feedback information includes pressure or force applied to the patient, depth of compression, compression rate (i.e., cycles per minute), duty cycle (i.e., portion of each cycle in which the patient is compressed), and the like. Such feedback information can be provided as discrete values, e.g., with gauges or digital readouts, or may be provided with a light or sound system which indicates when certain threshold values have been met or exceeded. It may be further desirable to provide a pacing signal, e.g., either a sound or flashing light, to facilitate maintaining a desired compression rate. Other features are further described in U.S. patent Ser. No. 13/554,986, previously incorporated by reference.

Figure 7:
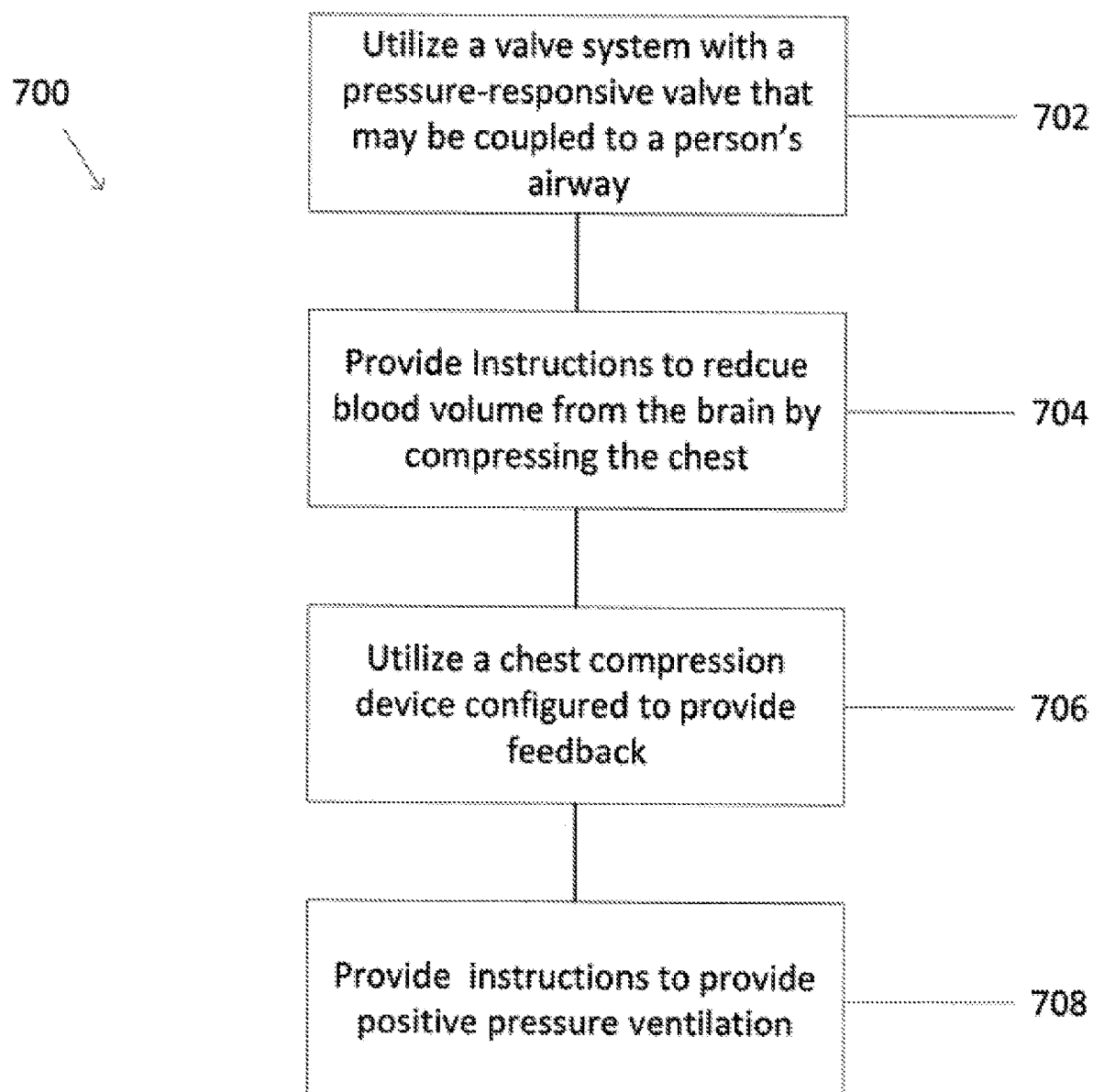
FIG. 7 is a flowchart showing a method to increase survival with favorable neurological function after cardiac arrest according to embodiments.

FIG. 7 depicts a method 700 to increase survival with favorable neurological function after cardiac arrest. The method may utilize a valve system having a pressure-responsive valve that may be configured to be coupled to a person's airway at block 702. The pressure-responsive valve may be configured to remain closed during successive chest compressions in order to permit removal at least about 100 ml from the lungs in order to lower intracranial pressure to improve survival with favorable neurological function. The method may also include providing instructions to increase blood volume to the brain by compressing the chest at a rate from about 80 to 120 per minute, and more preferably from about 90 to about 110 per minute, at a depth of about 4.5 to about 6 cm at block 704. The instructions may be provided by a guidance mechanism or system that visually and/or audibly instructions to rescuer on the proper rate and/or depth. In some embodiments, the valve system is further configured to remain closed during successive chest compressions in order to permit removal at least about 100 ml from the lungs in order to lower intracranial pressure to improve survival with favorable neurological function. The pressure-responsive valve is configured to remain closed until the negative pressure within the patient's airway reaches about −7 cm $H_2O$, at which time the pressure-responsive valve is configured to open to provide respiratory gases to flow to the lungs through the pressure-responsive valve. In some cases, the pressure-responsive valve is configured such that when it opens, it provides resistance to the incoming gas flow at a level of about 7 to about 18 cm $H_2O$ at a flow rate of 20 L/min. Optionally (as shown at block 706), the method may utilize a chest compression device that may be configured to provide user feedback as to whether the chest compressions are being performed at a rate between 80 to 120 compressions per minute (and more preferably from about 90 to 110 compressions per minute) and at a depth of 4.5 cm per compression to about 6 cm per compression. This may be achieved by using a load cell to measure force or an accelerometer to provide the feedback to the user in terms of the proper rate and depth of chest compressions. Feedback may include an audible sound produced by a speaker of the chest compression device and/or a visual indicator produced by a light or screen of the chest compression device. In some embodiments, the chest compression device may include an indicator configured to direct a user in compressing the patient's chest at the rate between 80 to 120 compressions per minute. Instructions are instruct the rescuer to provide positive pressure ventilation at a rate of 6 to 14 breaths/minute with a tidal volume of about 400 ml to about 700 ml at block 708. In some embodiments, the chest compression device may include an adhesive pad that is coupleable to the patient's chest. Instructions may also be given to actively decompress the patient's chest by pulling upward on the chest compression device in between at least some of the compressions. Also, it will be appreciated that the guidance features discussed above in connection with the chest compression device could optionally be included in a device or system separate from a chest compression device.

Example

A double-blind trial was conducted that compared the effectiveness of a sham (placebo) ITD with an active ITD. The inventor has unique access to the database based upon a contractual relationship with the researchers and Advanced Circulatory Systems. The sham ITD allowed for the free flow of respiratory gases to and from the lungs when performing chest compressions. The active ITD used was a ResQPOD® ITD as described in U.S. Pat. No. 8,408,204 and U.S. patent application Ser. No. 14/197,996, both of which were previously incorporated by reference. The trial included 8718 patients, with 4345 of the patients being randomly assigned treatment with a sham ITD and 4373 patients being randomly assigned to treatment with an active ITD. Standard manual closed chest CPR was performed. During the trial, chest compression rates varied between 50 and 240 per minute. Chest compression depth varied between 1 and 9 cm. Survival with favorable neurological function rates were highest when chest compression rates (in combination with the use of the active ITD) were within an optimal range between 90 and 110 chest compressions/min, with noticeably lower survival rates for patients receiving chest compressions at rates exceeding this range. In this trial, the ITD has a resistance of 16 mmHg. When the pressure within the thorax was <16 mmHg, the resistance valve within the ITD opened.

The mean compression depth for the patients was 41.9 mm, with the following ranges:

| Compression Depth | % of patients |
| --- | --- |
| <38 mm | 37 |
| 38-51 mm | 45 |
| >51 mm | 18 |

Figure 8:
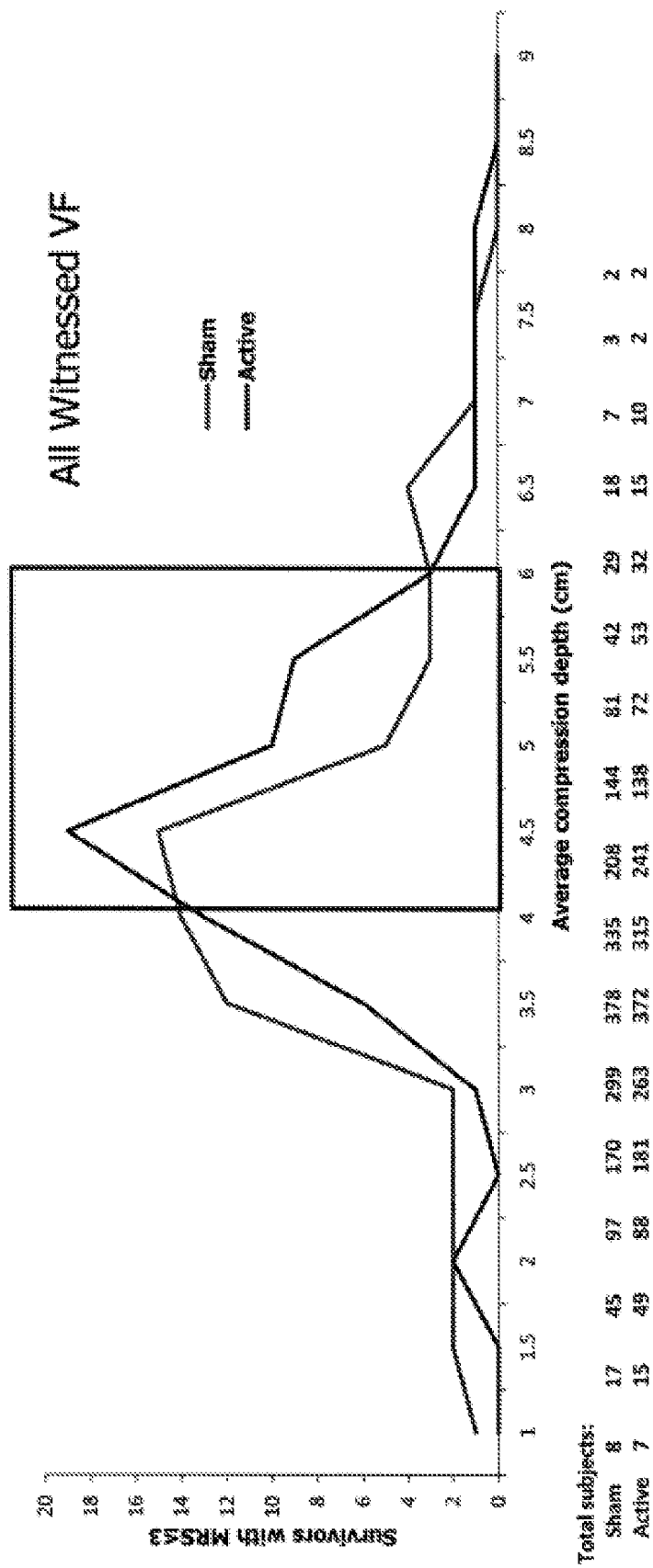
FIG. 8 is a line graph depicting the effect of compression depth on survival with good neurologic function, defined as a modified Rankin Scale (mRS) score <3.
Figure 9:
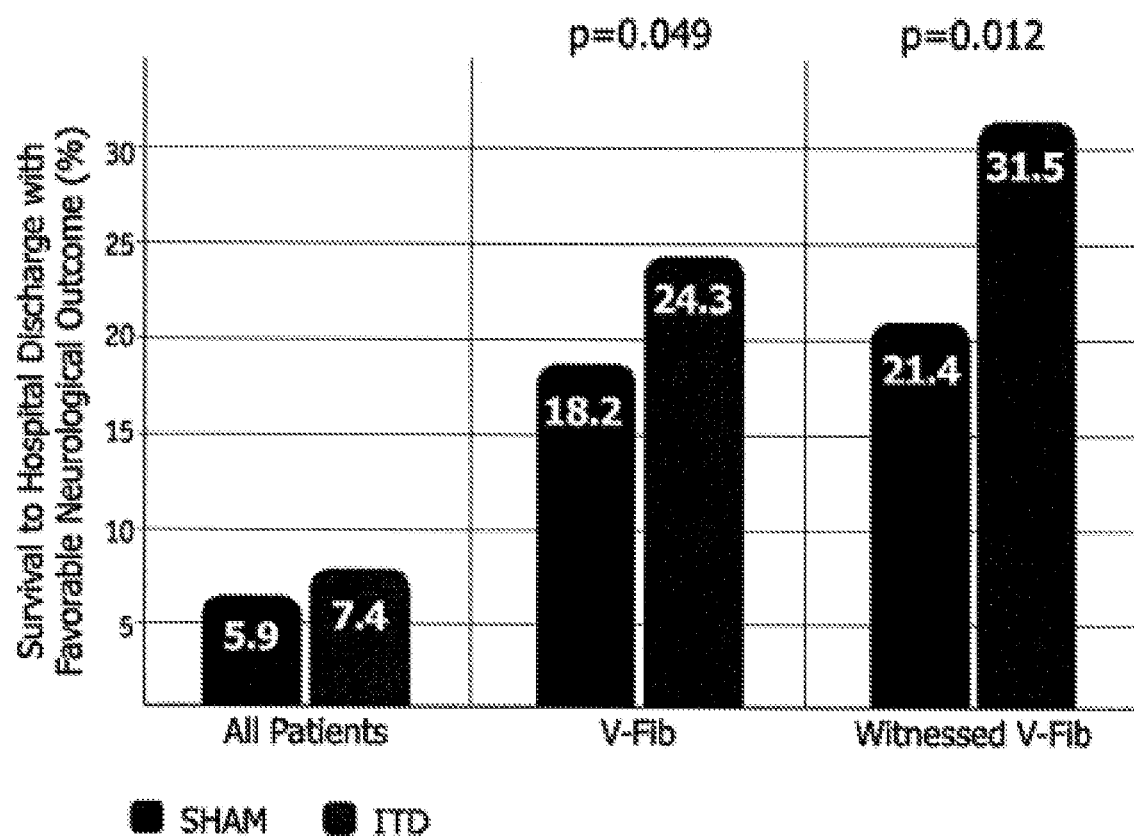
FIG. 9 is a bar graph depicting the effect of compression rate on survival with good neurologic function.

Maximum survival was associated with a compression depth of 45.8 mm, followed by a decline in survival by 50 mm, with an optimal interval of 44-49 mm. As seen in FIG. 8, the active ITD provides an increase in survival with good neurologic function over a sham ITD when used with chest compressions having a compression depth between about 4 cm and about 6 cm. FIG. 9 shows survival data for all patients receiving compression rates from 90 to 110 per minute, those patients who presented initially in (v-fib), and those patients who presented initially in witnessed v-fib.

Figure 10:
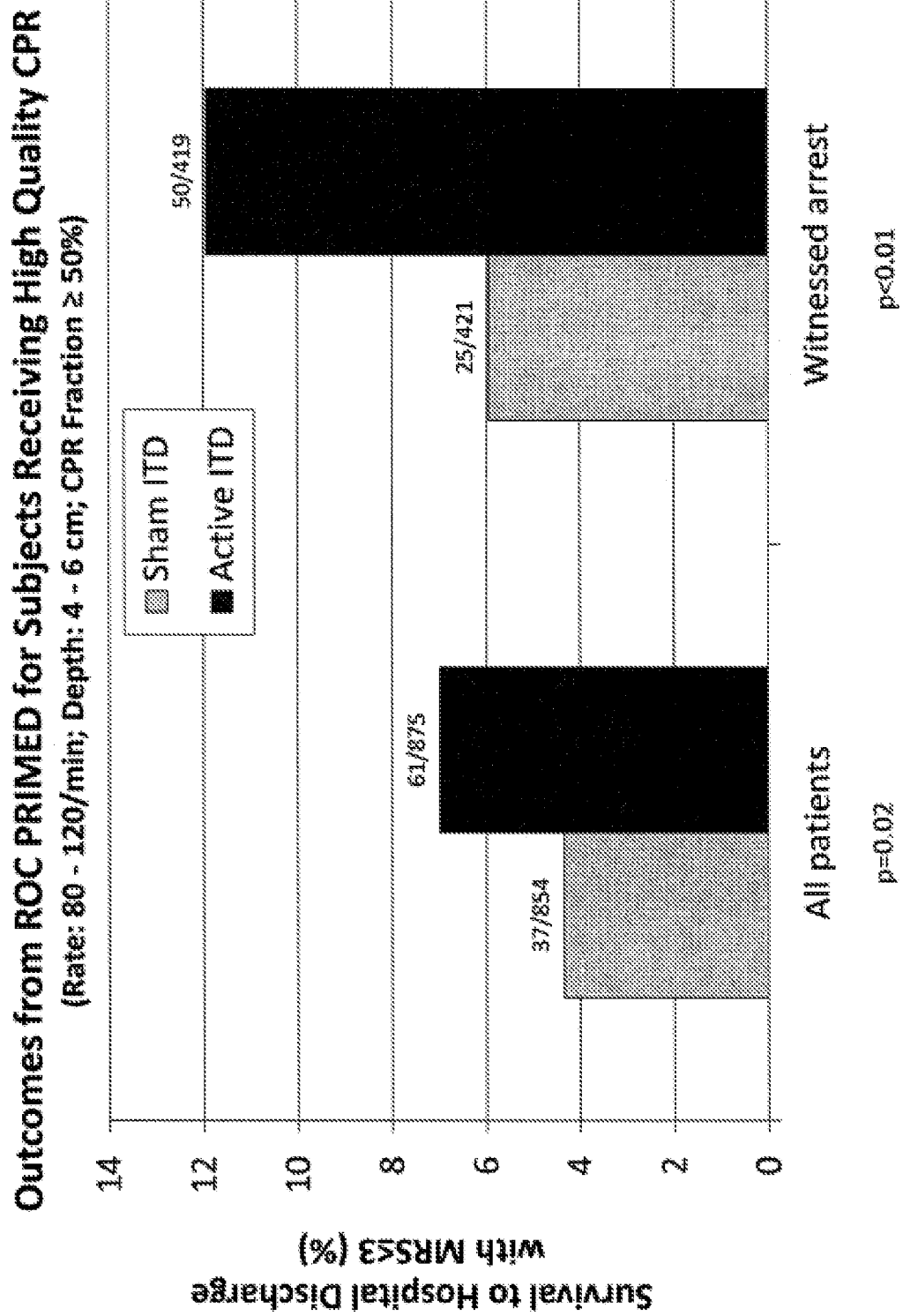
FIG. 10 is a bar graph depicting the effect of proper CPR on survival with good neurologic function.

Survival to hospital discharge with favorable neurological function increased significantly (34% in v-fib and 47% in witnessed v-fib) in patients treated with an active ITD when compared to the sham ITD. FIG. 10 focuses on survival in those patients who received an ITD and who had chest compression performed at the proper rate (in this Figure, between 80 and 120/min) and at the proper depth (in this Figure, between 4 cm and 6 cm). Those patients receiving an active ITD device showed significantly improved outcomes as compared to those receiving a sham ITD. Approximately 7% of all patients receiving an active ITD survived to hospital discharge with a favorable neurological state compared to slightly more than 4% of all patients receiving a sham ITD. Nearly 12% of patients presenting with witnessed arrest and receiving an active ITD survived to hospital discharge with a favorable neurological state compared to less than 6% of patients presenting with witnessed arrest that received a sham ITD.

Figure 11:
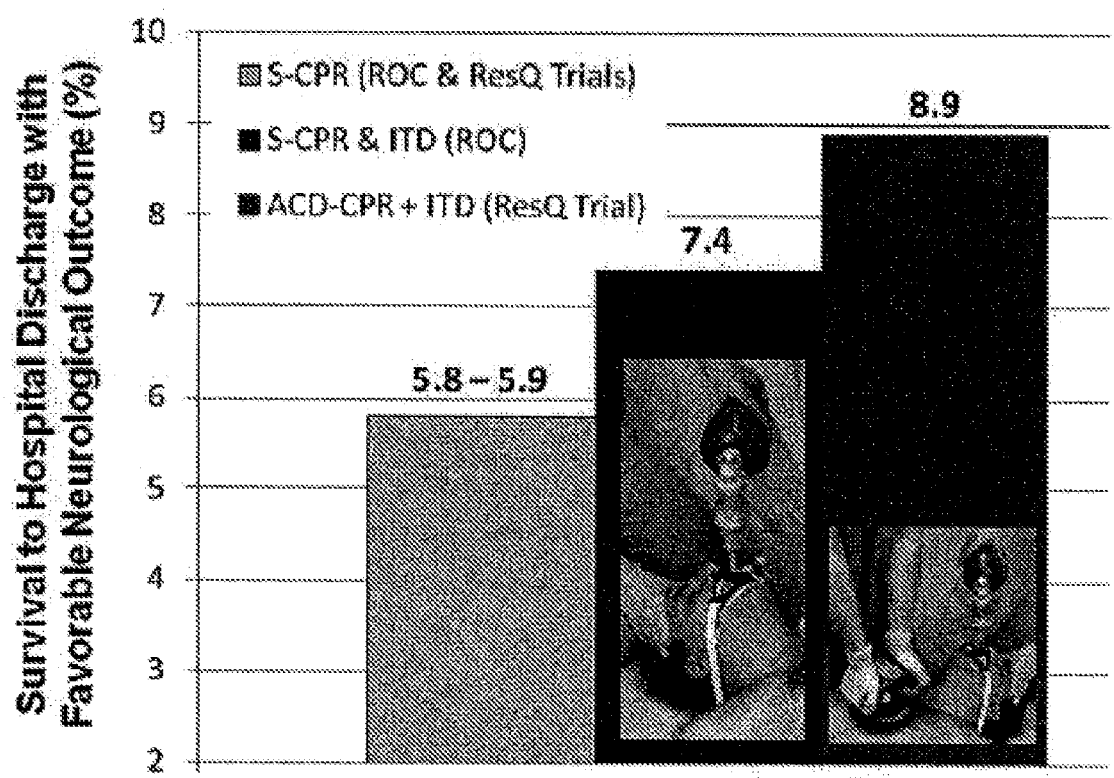
FIG. 11 is a bar graph depicting the benefit of an ITD compared with CPR alone.

FIG. 11 shows that standard CPR produces a 5.8%-5.9% survival to hospital discharge with favorable neurological outcome. When the active ITD was used with high quality standard CPR (chest compressions at 90-110 per minute at a depth of 4 cm to 6 cm), overall survival improved by 25% over the standard CPR, up to 7.4%. When the active ITD is used with ACD CPR, survival rates improve (by 53%) compared to standard CPR, up to 8.9%. Thus, improved survival rates with a good neurological state were found when using either properly administered standard CPR or ACD CPR in conjunction with an ITD as described herein.

Figure 12:
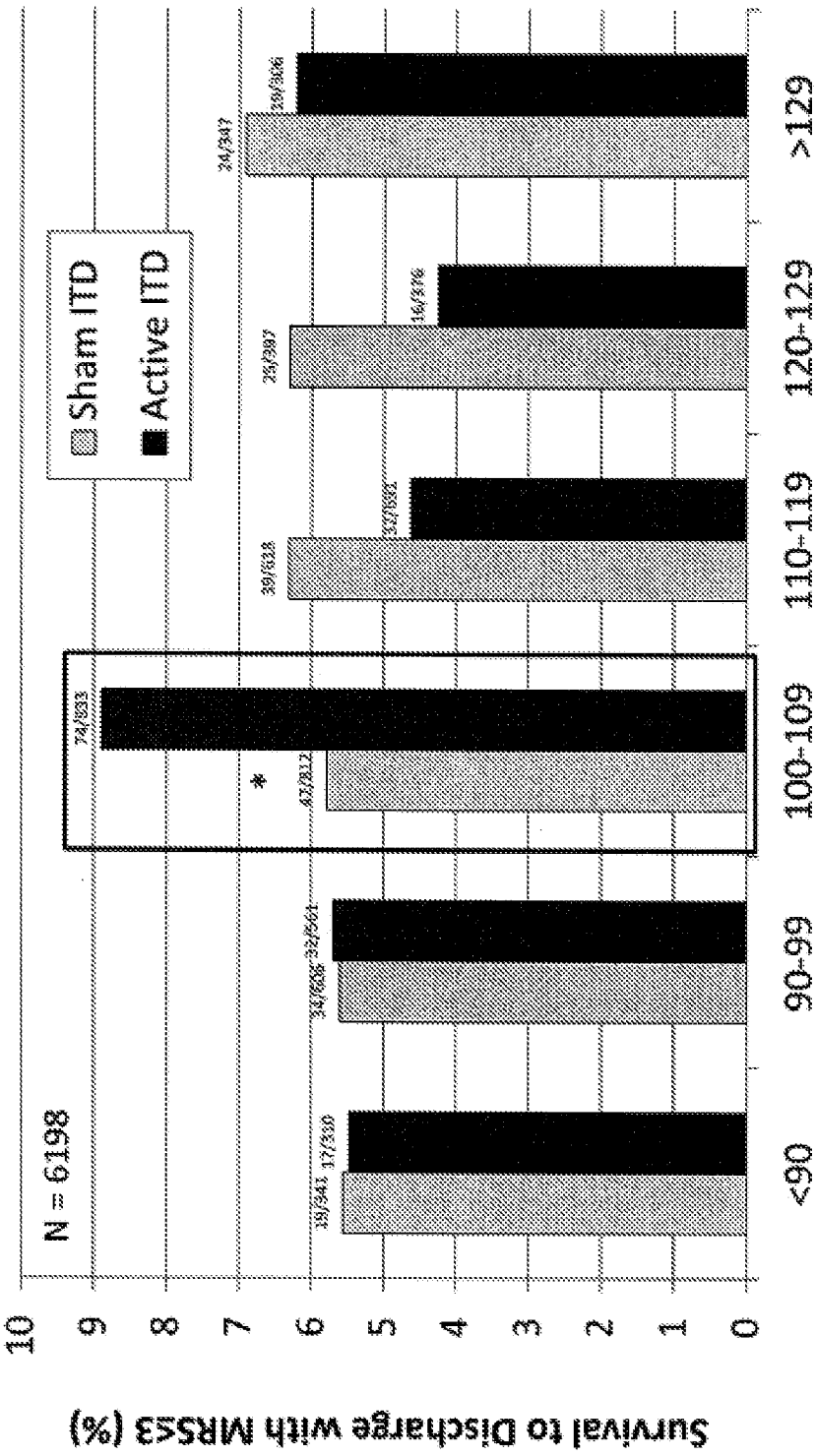
FIG. 12 is a bar graph depicting survival rates as a function of chest compression rate for all heart rhythms.
Figure 13:
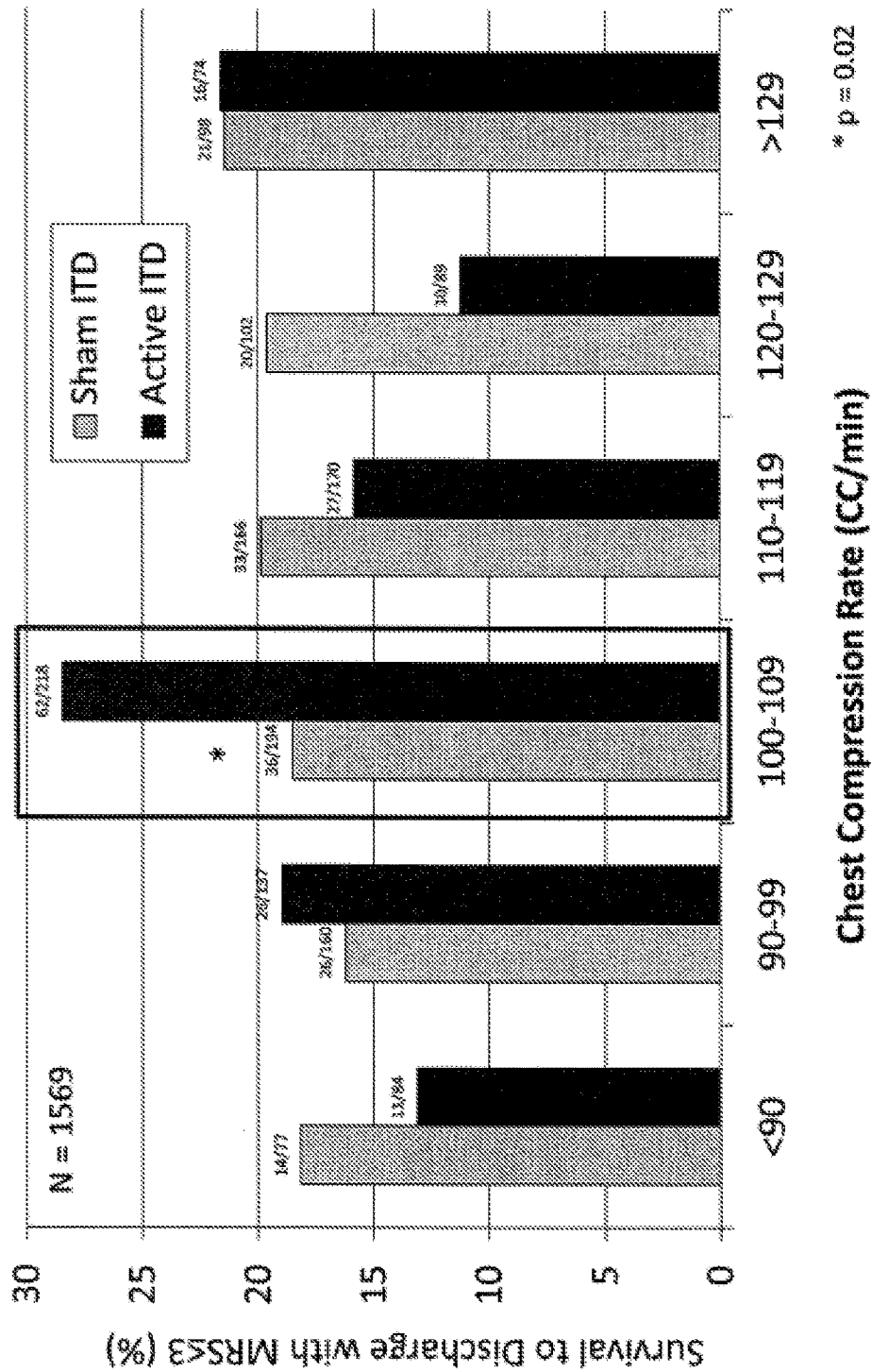
FIG. 13 is a bar graph depicting survival rates as a function of chest compression rate for shockable heart rhythms.

FIGS. 12 and 13 show the likelihood of survival to discharge with a favorable neurological state based on compression rate. This represents a new and unanticipated clinical finding. For example, FIG. 12 shows the survival to discharge for patients with all heart rhythms. Patients receiving an active ITD shows increased survival rates over sham ITD patients when chest compressions at a rate of between 90 and 110 per minute. Notably, patients receiving an active ITD and compressions between 100 and 110 per minute saw an approximately 50% increase in survival than those receiving a sham ITD and similar chest compression rates. By contrast, with a sham ITD, there was no ideal rate or "sweet spot" associated with a higher survival with favorable neurological function rate. This was only observed with the active ITD. FIG. 13 shows the survival to discharge for patients with shockable heart rhythms. Patients receiving an active ITD shows increased survival rates over sham ITD patients when chest compressions at a rate of between 90 and 110 per minute.

Figure 14:
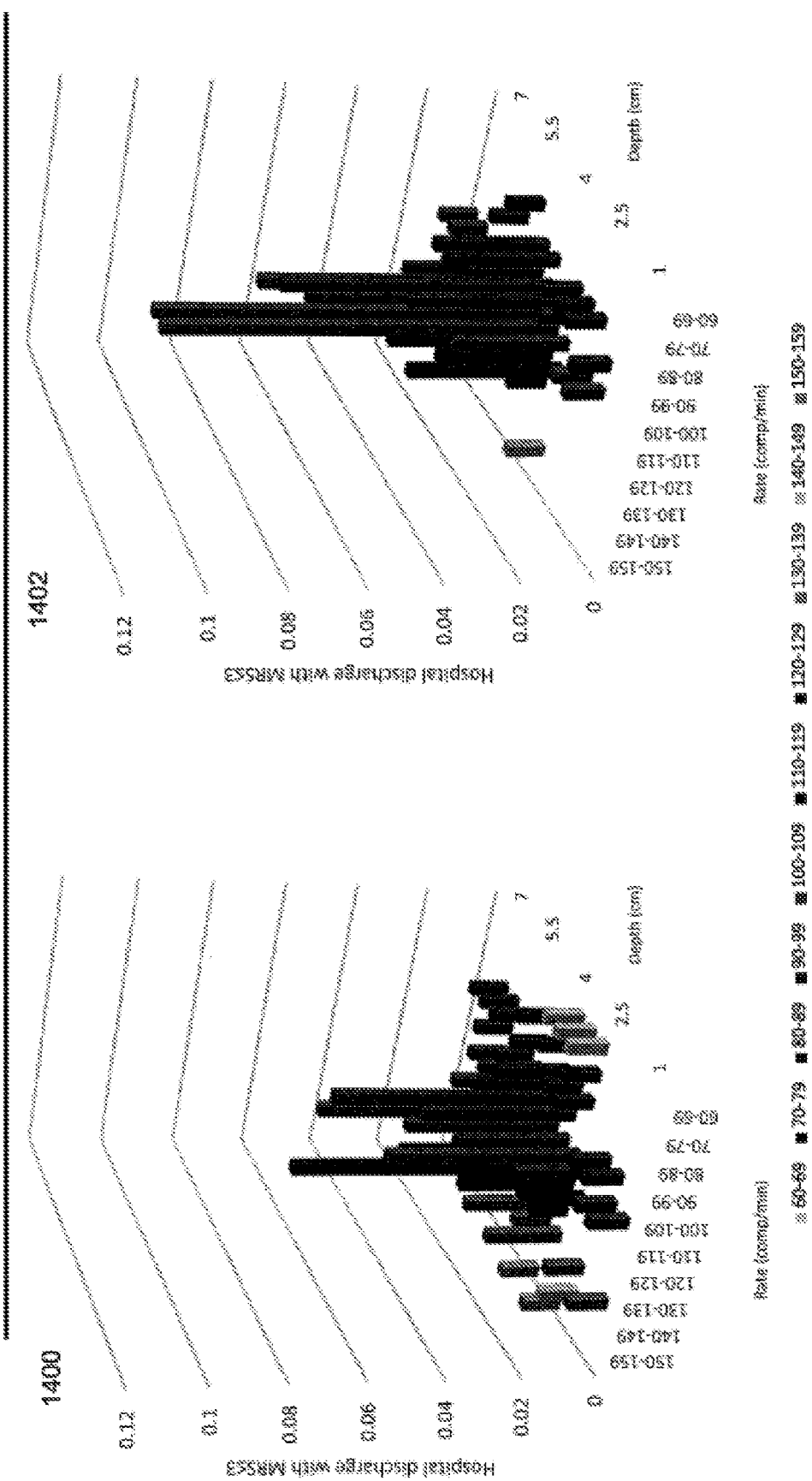
FIG. 14 is a bar graph depicting the effectiveness of administration of proper CPR in conjunction with an ITD.

FIG. 14 demonstrates the importance of proper chest compression rates and depths in conjunction with an ITD device to increase the odds of survival with good neurological function. This figure shows the novel finding that chest compression rate and depth and the active ITD but not the sham ITD interact in a unique way with standard manual closed chest CPR. Survival with favorable brain function, shown in the bar graph 1400, varied widely when the sham ITD was used over a broad range of rate and depth. Bar graph 1402 shows these survival rates with favorable brain function for patients receiving active ITDs as a function of the compression depth and rate. By contrast to Bar graph 1400 with the sham ITD, with the active ITD shown in bar graph 1402, there was a narrow range of rate and depth where highest survival rates are seen where the depth and rate are between about 4 cm to about 6 cm and 90 and 110 per minute, respectively. The survival rates are noticeably higher with the active ITD than with the sham ITD results of bar graph 1400.

The invention has now been described in detail for purposes of clarity and understanding. However, it will be appreciated that certain changes and modifications may be practiced within the scope of the appended claims.

The invention claimed is:

1. A system for providing treatment to a patient experiencing cardiac arrest, the system comprising:
   a guidance device configured to provide feedback for a user to compress the patient's chest according to at least one target rate that falls within a range of between about 80 compressions per minute and about 120 compressions per minute, and according to at least one target depth that falls within a range of between about 4 centimeters per compression and about 6 centimeters per compression; and
   a pressure-responsive valve adapted to be coupled to the patient's airway, the pressure-responsive valve being configured to:
      remain closed when negative pressure within the patient's airway fails to meet a threshold value, to prevent gas from entering the patient's lungs during successive chest compressions and to permit exit of at least about 200 mL of gas from the patient's lungs, and
      open when negative pressure within the patient's airway reaches the threshold value to permit gas flow to the patient's lungs through the pressure-responsive valve.

2. The system according to claim 1, wherein the threshold value falls within a range of about −7 cmH$_2$O and −18 cmH$_2$O.

3. The system according to claim 1, wherein the guidance device comprises a chest compression device.

4. The system according to claim 3, wherein the chest compression device further comprises:
   a handle; and
   an adhesive pad that is coupleable to the handle and to the patient's chest such that by pulling upward on the chest compression device, the user may actively decompress the patient's chest.

5. The system according to claim 4, wherein the handle is coupleable to the adhesive pad by a magnetic coupling.

6. The system according to claim 5, wherein the magnetic coupling is configured such that the handle decouples from the adhesive pad when a decompression force above a predetermined threshold is applied to the handle.

7. The system according to claim 3, wherein the chest compression device is configured to provide chest compressions at a depth of between about 4.5 cm per compression to about 6 cm per compression.

8. The system of claim 3, wherein the chest compression device is a manual chest compression device.

9. The system of claim 8, wherein the manual chest compression device is an active compression decompression device.

10. The system according to claim 3, wherein the chest compression device comprises one or more of a load cell and an accelerometer.

11. The system according to claim 1, wherein the guidance device comprises one or more of a speaker, a light emitting diode, and a display.

12. The system according to claim 11, wherein the feedback comprises one or more of an audible indicator and a visual indicator.

13. The system according to claim 12, wherein the visual indicator is a light, and wherein the light is produced at a rate that indicates when chest compressions should be provided.

14. The system according to claim 12, wherein the audible indicator is produced at a rate that indicates when chest compression should be provided.

15. The system according to claim 1, wherein the guidance device comprises a graphical user interface.

16. The system according to claim 15, wherein the graphical user interface comprises one or more inputs corresponding to patient size.

17. The system according to claim 15, wherein the graphical user interface is configured to display one or more of a target chest compression rate, a target chest decompression rate, an actual chest compression rate, a target chest decompression rate, a target chest compression force, a target chest decompression force, an actual chest compression force, and/or an actual chest decompression force.

18. The system according to claim 17, wherein the graphical user interface comprises a warning indicator configured to provide the user with an indication that an actual chest compression rate, actual chest decompression rate, actual chest compression force, and/or actual chest decompression force exceeds a predetermined difference from the target chest compression rate, target chest decompression rate, target chest compression force, and/or target chest decompression force.

19. The system according to claim 1, wherein the removal of air from the patient's lungs decreases intracranial pressure in the patient and improves survival with favorable neurological function.

20. The system according to claim 1, further comprising a positive pressure ventilation device.

\* \* \* \* \*